(12) United States Patent
Afonso et al.

(10) Patent No.: US 10,441,187 B2
(45) Date of Patent: *Oct. 15, 2019

(54) SYSTEM AND METHOD FOR DIAGNOSING ARRHYTHMIAS AND DIRECTING CATHETER THERAPIES

(71) Applicant: St. Jude Medical, Atrial Fibrillation Division, Inc., St. Paul, MN (US)

(72) Inventors: Valtino X. Afonso, Oakdale, MN (US); Jiazheng Shi, Scottsdale, AZ (US); Steven J. Kim, New York, NY (US); D. Curtis Deno, Andover, MN (US); Dennis J. Morgan, Crystal, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/592,290

(22) Filed: May 11, 2017

(65) Prior Publication Data

US 2017/0311833 A1    Nov. 2, 2017

Related U.S. Application Data

(63) Continuation of application No. 14/881,849, filed on Oct. 13, 2015, now Pat. No. 9,675,266, which is a (Continued)

(51) Int. Cl.
*A61B 5/042* (2006.01)
*A61B 5/04* (2006.01)
(Continued)

(52) U.S. Cl.
CPC .......... *A61B 5/0422* (2013.01); *A61B 5/0044* (2013.01); *A61B 5/044* (2013.01); (Continued)

(58) Field of Classification Search
CPC .......... A61B 5/042; A61B 5/044; A61B 5/00; A61B 5/053; A61B 5/06; A61B 18/14
(Continued)

(56) References Cited

U.S. PATENT DOCUMENTS 5,579,764 A    12/1996  Goldreyer
6,226,542 B1    5/2001  Reisfeld
(Continued)

FOREIGN PATENT DOCUMENTS

WO    1994/015528    7/1994
WO    1996/025095    8/1996
(Continued)

*Primary Examiner* — Jon Eric C Morales
(74) *Attorney, Agent, or Firm* — Dykema Gossett PLLC

(57) ABSTRACT

An efficient system for diagnosing arrhythmias and directing catheter therapies may allow for measuring, classifying, analyzing, and mapping spatial electrophysiological (EP) patterns within a body. The efficient system may further guide arrhythmia therapy and update maps as treatment is delivered. The efficient system may use a medical device having a high density of sensors with a known spatial configuration for collecting EP data and positioning data. Further, the efficient system may also use an electronic control system (ECU) for computing and providing the user with a variety of metrics, derivative metrics, high definition (HD) maps, HD composite maps, and general visual aids for association with a geometrical anatomical model shown on a display device.

19 Claims, 22 Drawing Sheets

Related U.S. Application Data continuation of application No. 13/977,147, filed as application No. PCT/US2011/066100 on Dec. 20, 2011, now Pat. No. 9,186,081.

(60) Provisional application No. 61/428,549, filed on Dec. 30, 2010.

(51) Int. Cl.
| | |
|---|---|
| *A61B 5/00* | (2006.01) |
| *A61B 5/044* | (2006.01) |
| *A61B 5/0452* | (2006.01) |
| *A61B 5/06* | (2006.01) |
| *A61B 5/053* | (2006.01) |
| *A61B 18/14* | (2006.01) |
| *A61B 18/00* | (2006.01) |
| *A61B 34/20* | (2016.01) |
| *A61B 34/00* | (2016.01) |

(52) U.S. Cl.
CPC ........ *A61B 5/04017* (2013.01); *A61B 5/0452* (2013.01); *A61B 5/0538* (2013.01); *A61B 5/065* (2013.01); *A61B 5/066* (2013.01); *A61B 5/4836* (2013.01); *A61B 5/6852* (2013.01); *A61B 5/6855* (2013.01); *A61B 18/1492* (2013.01); *A61B 5/068* (2013.01); *A61B 34/20* (2016.02); *A61B 34/25* (2016.02); *A61B 2018/00577* (2013.01); *A61B 2018/00839* (2013.01); *A61B 2562/043* (2013.01); *A61B 2576/023* (2013.01)

(58) Field of Classification Search
USPC .................................................. 600/509, 523
See application file for complete search history.

(56) References Cited

U.S. PATENT DOCUMENTS

| | | | |
|---|---|---|---|
| 6,233,476 B1 | 5/2001 | Strommer et al. | |
| 6,301,496 B1 | 10/2001 | Reisfeld | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 9,186,081 B2 * | 11/2015 | Afonso | A61B 5/0422 |
| 2002/0165448 A1 | 11/2002 | Ben-Haim et al. | |
| 2007/0073179 A1 | 3/2007 | Afonso et al. | |
| 2009/0069704 A1 | 3/2009 | MacAdam | |
| 2009/0112106 A1 | 4/2009 | Zhang | |
| 2009/0124915 A1 | 5/2009 | MacAdam | |
| 2009/0275827 A1 | 11/2009 | Aiken et al. | |
| 2009/0281439 A1 | 11/2009 | Harlev et al. | |
| 2010/0204552 A1 | 8/2010 | Yamamoto et al. | |
| 2012/0092016 A1 | 4/2012 | Kruspe | |

FOREIGN PATENT DOCUMENTS

| | | |
|---|---|---|
| WO | 1996/039929 | 12/1996 |
| WO | 1997/024983 | 7/1997 |
| WO | 2006/037172 | 4/2006 |
| WO | 2007/035306 | 3/2007 |
| WO | 2007/137045 | 11/2007 |
| WO | 2007/146864 | 12/2007 |
| WO | 2008/138009 | 11/2008 |
| WO | 2010/042826 A1 | 4/2010 |
| WO | 2010/058372 | 5/2010 |

* cited by examiner

SYSTEM AND METHOD FOR DIAGNOSING ARRHYTHMIAS AND DIRECTING CATHETER THERAPIES

CROSS-REFERENCE TO RELATED APPLICATIONS

This application is a continuation of U.S. application Ser. No. 14/881,849, filed 13 Oct. 2015 (the '849 application), now U.S. Pat. No. 9,675,266, which is a continuation of U.S. application Ser. No. 13/977,147, filed 28 Jun. 2013 (the '147 application), now U.S. Pat. No. 9,186,081, which is a national stage application of international application no. PCT/US2011/066100, filed 20 Dec. 2011 (the '100 application), which in turn claims the benefit of U.S. application No. 61/428,549, filed 30 Dec. 2010 (the '549 application). The '849 application, '147 application, the '100 application and the '549 application are each hereby incorporated by reference as though fully set forth herein.

BACKGROUND OF THE INVENTION a. Field of the Invention

The instant disclosure relates to a system employing a medical device, such as, for example, a catheter, for diagnostic, therapeutic, and/or ablative procedures. More specifically, the instant disclosure relates to a system for measuring, classifying, analyzing, and mapping spatial electrophysiological patterns and for guiding arrhythmia therapy.

b. Background Art

The human heart muscle routinely experiences electrical currents traversing its many surfaces and ventricles, including the endocardial chamber. Just prior to each heart contraction, the heart muscle is said to "depolarize" and "repolarize," as electrical currents spread across the heart and throughout the body. In healthy hearts, the surfaces and ventricles of the heart will experience an orderly progression of a depolarization wave. In unhealthy hearts, such as those experiencing atrial arrhythmia, including for example, ectopic atrial tachycardia, atrial fibrillation, and atrial flutter, the progression of the depolarization wave may not be so orderly. Arrhythmias may persist as a result of scar tissue or other obstacles to rapid and uniform depolarization. These obstacles may cause depolarization waves to repeat a circuit around some part of the heart. Atrial arrhythmia can create a variety of dangerous conditions, including irregular heart rates, loss of synchronous atrioventricular contractions, and stasis of blood flow, all of which can lead to a variety of ailments and even death.

Medical devices, such as, for example, electrophysiology (EP) catheters, are used in a variety of diagnostic and/or therapeutic medical procedures to correct such heart arrhythmias. Typically in a procedure, a catheter is manipulated through a patient's vasculature to a patient's heart, for example, and carries one or more electrodes that may be used for mapping, ablation, diagnosis, and/or to perform other functions. Once at an intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to, from, and at the treatment site, which can invariably be a function of a user's skill level.

Before or during an ablation procedure, however, a user must measure and diagnose these undesirable electrical pathways and regions of arrhythmia "breakout." An electrogram, used to help identify these regions, is any record of change in electric potential over time, often obtained by placing an electrode directly on or near the surface of the heart tissue. To acquire electrograms, conventional techniques include point-by-point methods of recording changes in electrical potential. These changes in potential may then be mapped onto a corresponding model of an anatomical structure. In other words, these methods enable the creation of electrocardiographic maps by navigating one or more catheters around an area of interest and collecting electrogram and spatial localization data from one spot to the next and then mapping the collected data accordingly.

A depolarization wave is detected on a signal from catheters to create maps such as Local Activation Time (LAT) and Peak to Peak (PP) voltage maps. In addition to being laborious and time consuming, these methods assume that a mapped electrogram is the result of only one depolarization. As a result, additional depolarizations, which commonly occur in complex arrhythmias, are not represented. Still further, due to the sequential nature of data acquisition, each electrogram of interest must then be time-aligned with a fixed fiducial reference.

Thus, conventional techniques and the resulting maps are not without drawbacks. As a further example, one map that is often created is a complex fractionated atrial electrogram (CFE) map. One type of CFE map documents mean cycle length or activation interval over a one to eight second period. A primary limitation of this type of CFE map is with its lack of specificity. Although any given electrogram may demonstrate CFE potentials, the underlying causes of the complex fractionated activity are unclear. And while the presence of complex fractionated activity suggests underlying anisotropy of conduction, this type of CFE map yields no direct information relating to underlying wavefront propagation patterns.

Accordingly, the inventors herein have recognized a need for improved systems and methods for acquiring a multitude of electrograms at the same time, and for a system that can provide a user with spatial maps that enable the user to view electrophysiological patterns and to determine the underlying causes of various arrhythmias that will minimize and/or eliminate one or more of the deficiencies in conventional systems.

SUMMARY OF THE INVENTION

It is desirable to identify the sources of cardiac arrhythmias based on electrophysiological (EP) data, particularly for systems performing diagnostic, therapeutic, and ablative procedures on a patient. EP data may come from intrinsic rhythms such as, for example, Sinus Rhythm, Atrial Flutter, and Atrial Fibrillation. EP data may also come from manual interventions such as pacing and induced arrhythmias, for example. The present disclosure provides a system and methods for measuring, classifying, analyzing, and mapping spatial and temporal EP patterns. Based on analyses of collected EP data, the disclosed system and methods also guide arrhythmia therapy by highlighting possible sources of arrhythmia.

In one embodiment, the disclosed system can measure data from the tissue of a patient's body by using a plurality of sensors disposed along a distal end of a medical device. As noted above, one exemplary type of data that may be measured is EP data. Further, the medical device may be positionable near, along, against, or within the tissue of the patient's body. One example of a sensor that may be used with the system is an electrode. A high density of sensors may be disposed along the distal end of the medical device to simultaneously measure voltages with respect to time (i.e., electrograms) from a region of the tissue. Because the sensors may be positioned proximal to one another and because the sensors may record data over a period of time, the disclosed system can perform a host of comparative spatial and temporal analyses.

The system may also comprise an electronic control unit (ECU) for collecting and analyzing the data measured by the plurality of sensors. The ECU, which may itself comprise a number of sub-components, can perform many functions as part of the system. For example, the ECU may acquire the measured data from the plurality of sensors positioned along the tissue. Using electric-field or magnetic-field based impedance techniques, the ECU may also determine the three-dimensional position coordinates of each sensor. In addition, the ECU may "know" the spatial arrangement of the plurality of sensors before the medical device is positioned near the tissue. In the alternative, the ECU may determine the spatial arrangement of sensors by computing the distances between each three-dimensional position coordinate. Accordingly, the ECU may know the positions and spatial arrangement of the sensors, the voltages at each sensor, and the times at which those voltages were measured. Based on this input data, the ECU may compute a variety of metrics, derivative metrics, and combination metrics. Several examples of the computed metrics may include, without limitation, absolute activation time (AAT), percentage fractionation index (PFI), continuous spatial index (CSI), conduction velocity, spatial gradients of depolarization amplitude, consistency metrics, and activation direction. Yet further, the ECU may also highlight areas of interest in the tissue based on the results of these computed metrics. Using automated or semi-automated (computer-aided) intelligent compute algorithms and using a signal processing method (e.g., Hilbert transform) the disclosed system and method can be applied to characterize waveform patterns (e.g., rotor, focus beat, planar, dispersed) over the plurality of sensors.

In one embodiment, a method of operating the system to analyze data may be described as follows. At least one of a plurality of sensors positioned on a distal end of a medical device measures data from the body tissue of a patient. The measured data may then be transmitted from at least one of the plurality of sensors to an ECU. The system, or in some embodiments, the ECU, may then determine the position of the plurality of sensors, or at least the position of one sensor. The system may also compute at least one metric based on the position of the sensor or positions of the sensors. In general, metrics are quantifications of data such as, for example and without limitation, EP data. Based on the position(s) of the sensor(s) and either the computed metric or the measured data, the system may then generate a map for display. After computing these and other metrics, derivations, and combinations thereof, the system may generate spatial maps of these metrics. In some embodiments, these maps may be superimposed onto a geometrical anatomical model representing the tissue. These spatial maps may be configured to be updated with each successive heartbeat, at the discretion of the user, or continuously.

Another aspect of the disclosed system and methods involves identifying depolarization wavefront patterns based on the spatial distribution of EP data or metric values. To do so, the ECU may be configured in one exemplary embodiment to apply a variety of matched spatial filters to compiled EP data values.

Still another aspect of the disclosed system and methods involves creating three-dimensional visual aids representing either electrogram voltage vectors or conduction velocity vectors. This type of three-dimensional display may be superimposed onto a geometrical anatomical model or may be displayed in a graphical format as well.

In general, the disclosed system and methods for measuring, classifying, analyzing, and mapping spatial EP patterns and for guiding arrhythmia therapy are more spatially significant than ever before. The system and method provide physicians with more straightforward diagnostic information. Further, the metrics and maps described herein are merely exemplary. The foregoing and other aspects, features, details, utilities, and advantages of the present disclosure will be apparent from reading the following description and claims, and from reviewing the accompanying drawings.

DETAILED DESCRIPTION OF THE INVENTION

Figure 1:
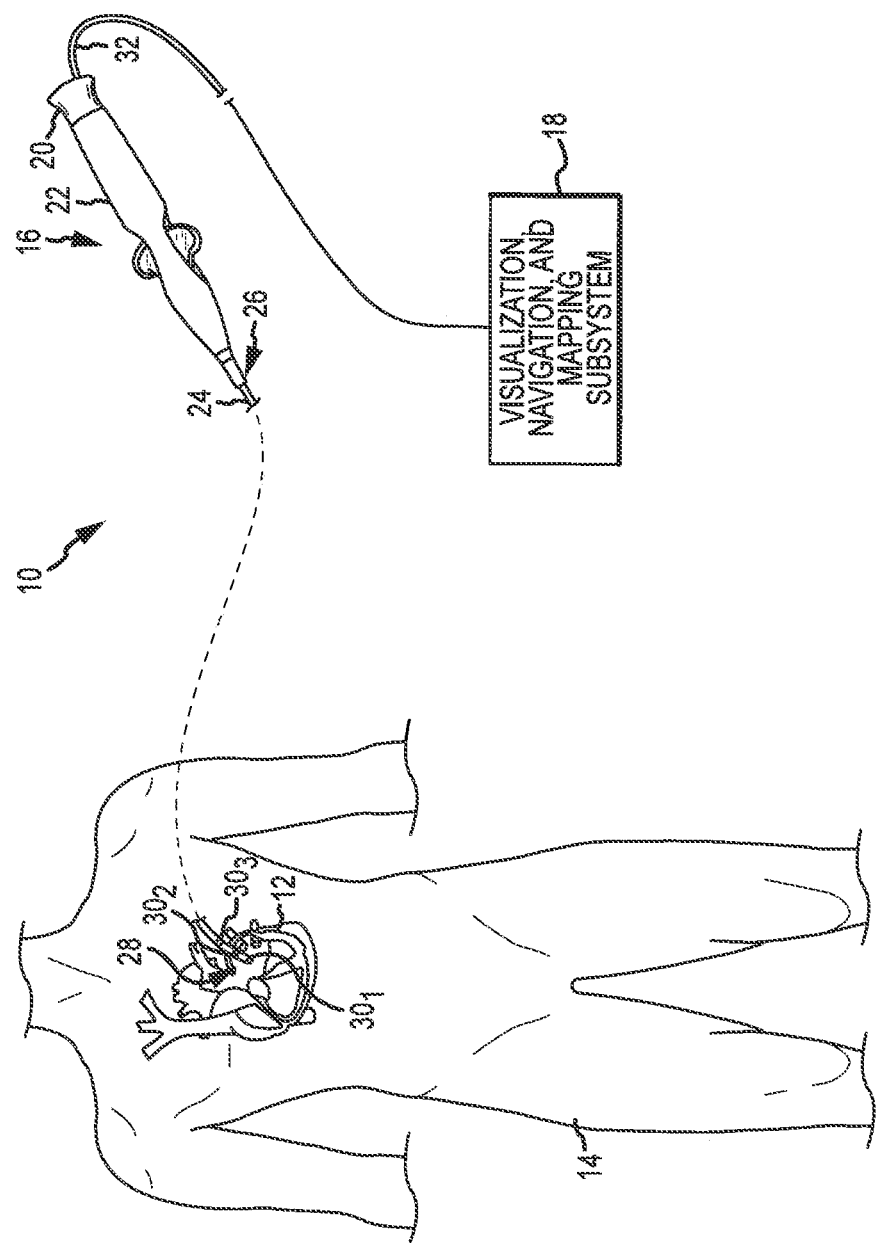
FIG. 1 is a schematic and diagrammatic view of a system for performing at least one of a diagnostic and a therapeutic medical procedure in accordance with present teachings.

Referring now to the drawings wherein like reference numerals are used to identify identical components in the various views, FIG. 1 illustrates one exemplary embodiment of a system 10 for performing one or more diagnostic and/or therapeutic functions on or for a tissue 12 of a body 14. In an exemplary embodiment, the tissue 12 comprises heart or cardiac tissue within a human body 14. It should be understood, however, that the system 10 may find application in connection with a variety of other tissues within human and non-human bodies, and therefore, the present disclosure is not meant to be limited to the use of the system 10 in connection with only cardiac tissue and/or human bodies.

The system 10 may include a medical device 16 and a subsystem 18 for the visualization, navigation, and/or mapping of internal body structures (hereinafter referred to as the "visualization, navigation, and mapping subsystem 18" or "subsystem 18").

In the exemplary embodiment of FIG. 1, the medical device 16 comprises a catheter, such as, for example, an electrophysiology catheter. In other exemplary embodiments, the medical device 16 may take a form other than a catheter, such as, for example and without limitation, a sheath or catheter-introducer, or a catheter other than an electrophysiology catheter. For clarity and illustrative purposes only, the description below will be limited to embodiments of the system 10 wherein the medical device 16 comprises a catheter (catheter 16).

The catheter 16 is provided for examination, diagnosis, and/or treatment of internal body tissues such as tissue 12. The catheter 16 may include a cable connector or interface 20, a handle 22, a shaft 24 having a proximal end 26 and a distal end 28 (as used herein, "proximal" refers to a direction toward the end of the catheter 16 near the handle 22, and "distal" refers to a direction away from the handle 22), and one or more sensors, such as, for example and without limitation, a plurality of electrodes 30 (i.e., $30_1, 30_2, \ldots, 30_N$), mounted in or on the shaft 24 of the catheter 16 at or near the distal end 28 of the shaft 24.

In an exemplary embodiment, each electrode 30 is configured to both acquire electrophysiological (EP) data corresponding to the tissue 12, and to produce signals indicative of its three-dimensional (3-D) position (hereinafter referred to as "positioning data"). In another exemplary embodiment, the catheter 16 may include a combination of electrodes 30 and one or more positioning sensors (e.g., electrodes other than the electrodes 30 or magnetic sensors (e.g., coils)). In one such embodiment, the electrodes 30 are configured to acquire EP data relating to the tissue 12, while the positioning sensor(s) is configured to generate positioning data indicative of the 3-D position thereof, which, as will be described below, may be used to determine the 3-D position of each electrode 30. In other embodiments, the catheter 16 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

The connector 20 provides mechanical and electrical connection(s) for one or more cables 32 extending, for example, from the visualization, navigation, and mapping subsystem 18 to the one or more electrodes 30 or the positioning sensor(s) mounted on the catheter 16. In other embodiments, the connector 20 may also provide mechanical, electrical, and/or fluid connections for cables extending from other components in the system 10, such as, for example, an ablation system and a fluid source (when the catheter 16 comprises an irrigated catheter). The connector 20 is conventional in the art and is disposed at the proximal end 26 of the catheter 16.

The handle 22 provides a location for a user to hold the catheter 16 and may further provide means for steering or guiding the shaft 24 within the body 14. For example, the handle 22 may include means to manipulate one or more steering wires extending through catheter 16 to the distal end 28 of the shaft 24 to steer the shaft 24. The handle 22 is also conventional in the art and it will be understood that the construction of the handle 22 may vary. In other embodiments, the control of the catheter 16 may be automated such as by being robotically driven or controlled, or driven and controlled by a magnetic-based guidance system. Accordingly, catheters controlled either manually or automatically are both within the spirit and scope of the present disclosure.

The shaft 24 is an elongate, tubular, and flexible member configured for movement within the body 14. The shaft 24 supports, for example and without limitation, the electrodes 30, other electrodes or positioning sensors mounted thereon, associated conductors, and possibly additional electronics used for signal processing or conditioning. The shaft 24 may also permit transport, delivery and/or removal of fluids (including irrigation fluids, cryogenic ablation fluids, and body fluids), medicines, and/or surgical tools or instruments. The shaft 24, which may be made from conventional materials such as polyurethane, defines one or more lumens configured to house and/or transport electrical conductors, fluids, or surgical tools. The shaft 24 may be introduced into a blood vessel or other structure within the body 14 through a conventional introducer. The shaft 24 may then be steered or guided through the body 14 to a desired location such as the tissue 12 using means well known in the art.

The distal end 28 of the shaft 24 may be the main portion of the catheter 16 that contains the electrodes 30 or other sensors for acquiring EP data and positioning data. As described above, in one embodiment, the electrodes 30 may be configured to acquire both EP data and positioning data. In another embodiment, and as will be described in greater detail below, the electrodes 30 may be configured to acquire EP data while one or more positioning sensors may be configured to acquire positioning data, which may then be used to determine the respective positions of the electrodes 30. Regardless of whether the positioning data is acquired by the electrodes 30 or by positioning sensors, the distal end 28 may be arranged in a number of configurations that facilitate the efficient acquisition, measurement, collection, or the like of EP data from the tissue 12.

Figure 2:
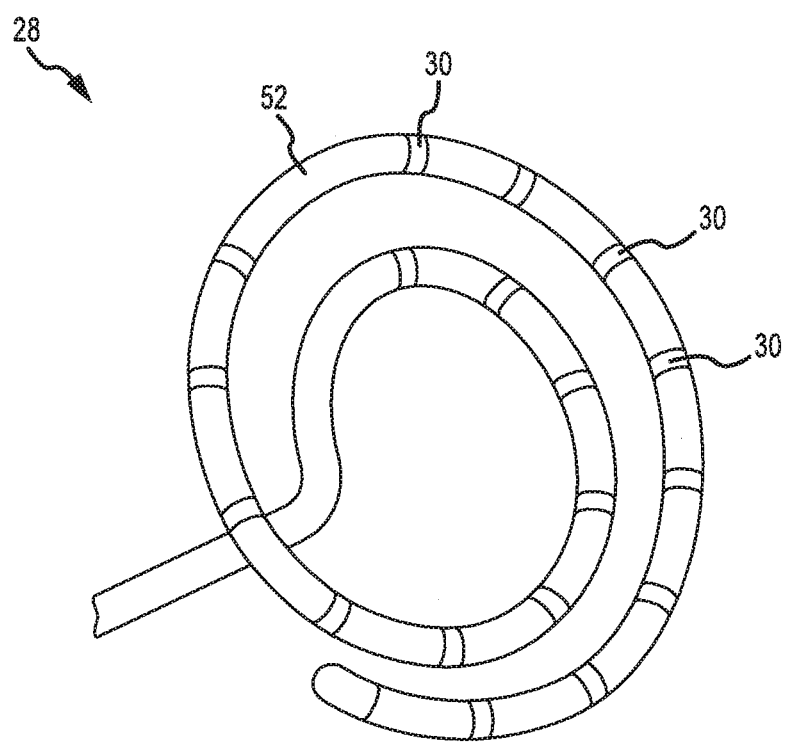
FIG. 2 is an isometric view of a distal end of an exemplary embodiment of a medical device arranged in a spiral configuration.

In one embodiment, as shown in FIG. 2, the distal end 28 may be arranged in a spiral configuration. In this embodiment, the spiral configuration may be generally planar and may contain a high density of electrodes 30 for taking unipolar or bipolar measurements of EP data from the tissue 12. Unipolar measurements may generally represent the electrical voltage perceived at each electrode. Bipolar measurements, though, may generally represent the electrical potential between any pair of electrodes. And as one skilled in the art will recognize, bipolar measurements may be computed from unipolar measurements. Moreover, the electrodes 30 may be disposed in or along the distal end 28 in a known spatial configuration such that the distances between the electrodes 30 are known. The diameters of the loops, such as loop 52, may vary from one embodiment to another. In one exemplary embodiment, the diameter of the outermost loop is twenty millimeters. In an alternative embodiment, the spiral configuration may contain multiple spiral loops.

There are many advantages to placing a high density of electrodes 30 on the spiral configuration or at the distal end 28 of any catheter 16. Because the distribution of electrodes 30 is dense, and because of the multitude of possible unipolar and bipolar comparisons of the electrodes 30, the spiral configuration may be ideal for creating high definition (HD) surface maps representative of electrical activity on the tissue 12.

Figure 3:
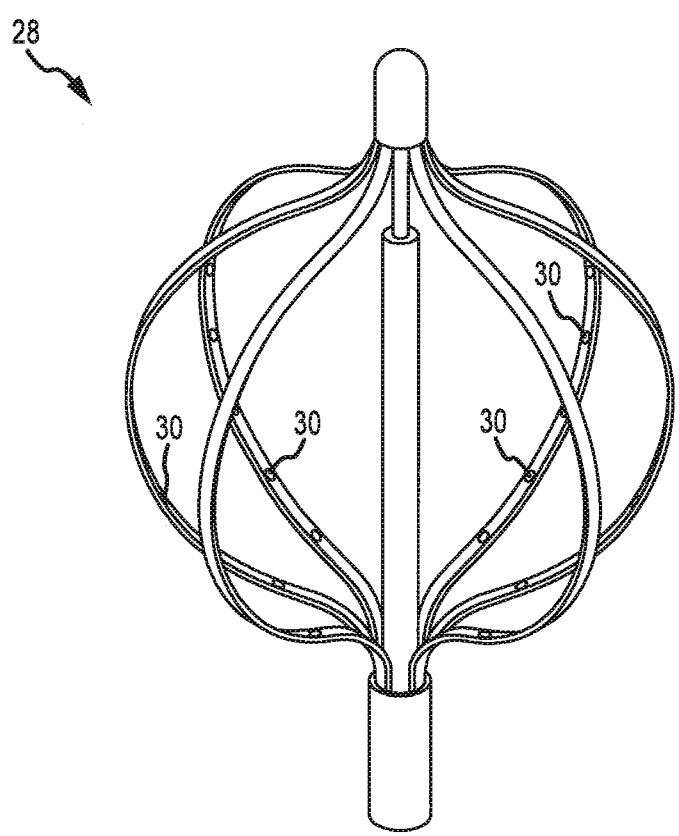
FIG. 3 is an isometric view of a distal end of another exemplary embodiment of a medical device arranged in a basket configuration.

In another embodiment, as shown in FIG. 3, the distal end 28 may be arranged in a basket configuration. The basket configuration, or a similar configuration with a generally cylindrical array of electrodes 30, may contain a high density of electrodes 30. In one embodiment, the electrodes 30 may be non-contact electrodes that generally need not be in contact with the tissue 12 to measure EP data. In another embodiment, the electrodes 30 may include both contact and non-contact electrodes.

Such non-contact electrodes may be used for unipolar analyses. It may be advantageous to analyze unipolar EP data since a unipolar electrogram morphology may provide more information regarding colliding wavefronts (presence of "R" waves in the QRS Complex known in the art), short radius reentry wavefronts (presence of the sinusoid waveform), and source wavefronts (a "QS" morphology on the electrogram at the onset of depolarization). In general, a depolarization wavefront is a group of electrical vectors that traverse the tissue 12 of the body 14. As described in more detail below, depolarization wavefronts may vary in pattern, size, amplitude, speed, and the like. And some depolarization wavefronts may be relatively orderly while others may be relatively, or even entirely, disorderly.

In another embodiment, however, bipolar EP data may provide better spatial localization data, better depolarization wave directionality indications, and better alternating current (AC) electrical noise rejection. With bipolar EP data, a pair of electrodes 30 (commonly referred to as "poles" or "bi-poles") may be spaced apart, but positioned relatively close together with respect to electric fields caused by other remote parts of the body 14. Thus, effects from remote electric fields may be negated since the electrodes 30 are positioned close to one another and experience similar effects from the distant electric field.

Figure 4A:
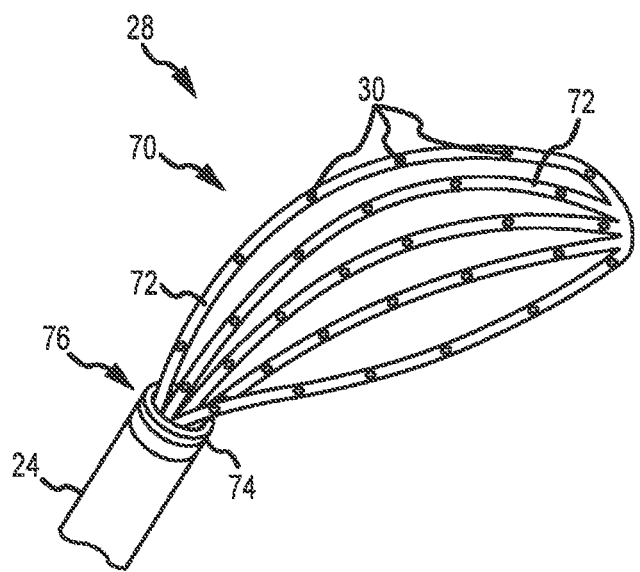
FIGS. 4*a*-4*b* are isometric and a side views, respectively, of a distal end of an exemplary embodiment of a medical device arranged in a matrix-like configuration.
Figure 4B:
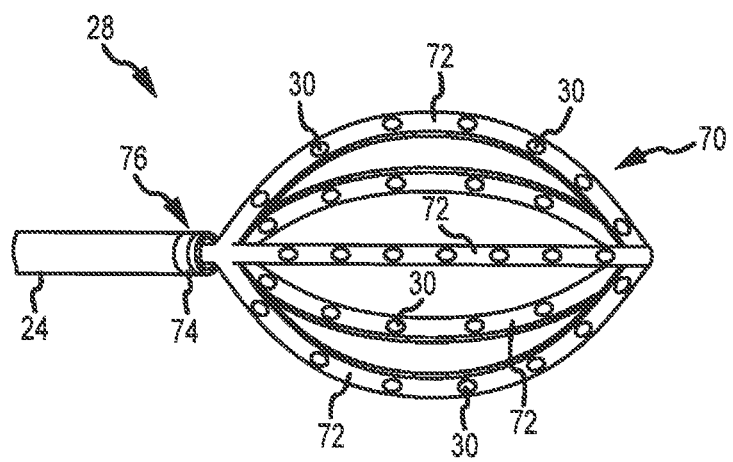

In yet another embodiment of the distal end 28 shown in FIGS. 4a-4b, a matrix-like configuration may also be provided with a high density of electrodes 30. FIG. 4a shows an isometric view of the matrix-like configuration, while FIG. 4b shows a side view. The matrix-like configuration may have a number of splines 72 arranged side by side, with each spline 72 having at least one electrode 30 mounted thereon. Longer splines may contain more electrodes 30 to maintain a consistent electrode density throughout the matrix-like configuration.

In the embodiment shown in FIGS. 4a-4b, the matrix-like configuration may be cupped, almost as if to have a slight scoop as seen in FIG. 4a. In another embodiment (not shown), the matrix-like configuration may be substantially flat or planar, without any scoop-like feature. While both embodiments may facilitate data measurements from the tissue 12, the matrix-like configuration shown in FIG. 4a in particular may be used to acquire at least some non-contact measurements. Another possible use of the matrix-like configuration would be to help diagnose arrhythmias and direct epicardial ablation therapies in the pericardial space.

In one embodiment, the matrix-like configuration along with other configurations of the distal end 28 may collapse to a streamlined profile for insertion, manipulation, and removal from the body 14. In addition, or in the alternative, the distal end 28 may be at least partially concealed and transported within the shaft 24 when not collecting data or performing a procedure. The shaft 24 may be more streamlined than the distal end 28, and therefore may provide a better vehicle for transporting the distal end 28 to and from the tissue 12. Once at the intended site, the distal end 28 may be deployed from the shaft 24 to perform the intended procedures. Likewise, after the procedures are performed, the distal end 28 may be re-concealed, at least in part, within the shaft 24 for removal from the body 14.

One exemplary way in which the matrix-like configuration is collapsible into a streamlined profile or fully or partially deployable is to allow the outer splines 72 to translate modestly within the shaft 24 while anchoring the innermost splines 72 to the shaft 24 at a point 74 at the distal end 28 thereof. Moreover, for enhanced functionality, a joint 76 may be incorporated near the point 74, either for providing flexibility or for selectively deflecting the distal end 28, thereby allowing the distal end 28 better access to the tissue 12.

Figure 5:
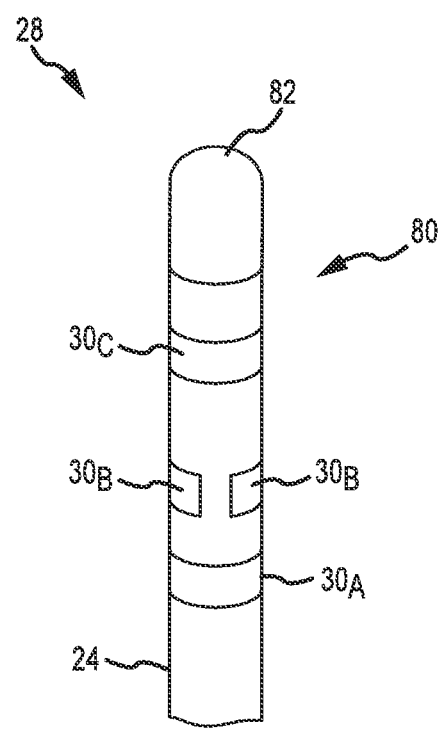
FIG. 5 is a top view of a distal end of an exemplary embodiment of a medical device wherein the medical device is a radio frequency (RF) ablation catheter.

Another exemplary embodiment of a high-density electrode catheter is illustrated in FIG. 5. In this embodiment, the distal end 28 comprises an ablation tip 80, and may be well suited for enhancing radio frequency (RF) ablation procedures. More particularly, the arrangement may allow for the provision of rapid positioning feedback and may also enable updates to be made to HD surface maps as the ablative procedures are being performed.

With continued reference to FIG. 5, in an exemplary embodiment wherein, as will be described below, the visualization, navigation, and mapping subsystem 18 is an electric field-based system, the distal end 28 may include a proximal ring electrode $30_A$ positioned close to, yet spaced apart from, a series of spot or button electrodes $30_B$. The proximal ring electrode $30_A$ and the spot electrodes $30_B$ may be used to acquire both EP data and positioning data. Spaced further distally from the spot electrodes $30_B$, a distal ring electrode $30_C$ may be disposed in or on the shaft 24 so that bipolar measurements of EP data may be made between the spot electrodes $30_B$ and the distal ring electrode $30_C$. Finally, the distal end 28 further includes an ablation electrode 82 for performing ablation therapies, such as, for example and without limitation, RF ablation therapies.

The visualization, navigation, and mapping subsystem 18 may determine the positions of the proximal ring electrode $30_A$ (or a geometric center thereof), the spot electrodes $30_B$, and the distal ring electrode $30_C$ (or a geometric center thereof) in the same manner as the position(s) of the electrode(s) 30 shown in FIG. 6, as will be described in greater detail below. Based on these positions and/or the known configuration of the distal end 28 (e.g., the spacing of the various electrodes), the position of the ablation electrode 82 may also be determined and, in certain embodiments, projected onto a geometrical anatomical model.

By incorporating at least three non-co-linear electrodes as is illustrated, for example, in FIG. 5, rotational information about the distal end 28 (referred to as "orientation") may be calculated. Hence six degrees of freedom (three for position and three for orientation) may be determined for the ablation tip 80 of the catheter 16. Knowing the position and orientation of the distal end 28 allows for a much simpler registration of coordinates into a body coordinate system, as opposed to a coordinate system with respect to the catheter itself.

In another embodiment wherein the visualization, navigation, and mapping subsystem 18 comprises a magnetic field-based system, the distal end 28 may include at least one magnetic field sensor—e.g., magnetic coils (not shown). If two or more magnetic field sensors are disposed near the ablation electrode 82, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self contained.

In yet another embodiment of the distal end 28 illustrated in FIG. 5, the distal ring electrode $30_C$ may be omitted and the spot electrodes $30_B$ may be located in its place. As a result, the spot electrodes $30_B$ would be closer to the ablation electrode 82, which would provide positioning coordinates closer to the ablation electrode 82. This in turn may provide for more accurate and precise calculation of the position of the ablation electrode 82. Additionally, just as if the distal ring electrode $30_C$ were still in place, a mean signal from the spot electrodes $30_B$ and the proximal ring electrode $30_A$ could still be used to obtain bipolar EP data.

Figure 6:
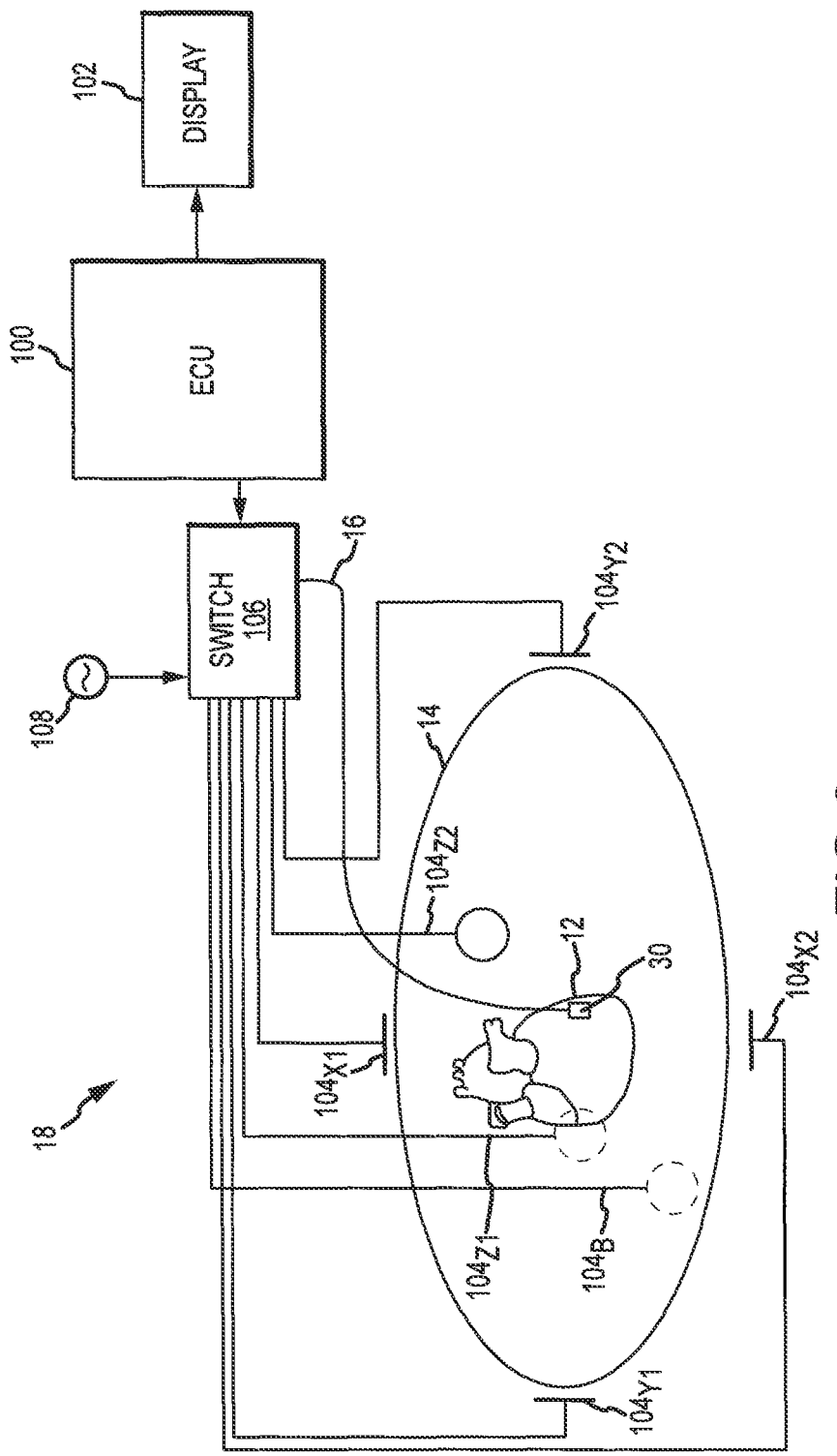
FIG. 6 is a schematic and diagrammatic view of an exemplary embodiment of a visualization, navigation, and mapping subsystem of the system illustrated in FIG. 1.

With reference to FIGS. 1 and 6, the visualization, navigation, and mapping subsystem 18 will now be described. The visualization, navigation, and mapping subsystem 18 is provided for visualization, navigation, and/or mapping of internal body structures and/or medical devices. In an exemplary embodiment, the subsystem 18 may contribute to the functionality of the system 10 in two principal ways. First, the subsystem 18 may provide the system 10 with a geometrical anatomical model representing at least a portion of the tissue 12. Second, the subsystem 18 may provide a means by which the position coordinates (x, y, z) of the electrodes 30 (or generally, sensors) may be determined as they measure EP data for analyses performed as part of the system 10. In certain embodiments, positioning sensors (e.g., electrical-field based or magnetic-field based) that are fixed relative to the electrodes 30 are used to determine the position coordinates. The positioning sensors provide the subsystem 18 with positioning data sufficient to determine the position coordinates of the electrodes 30. In other embodiments, position coordinates may be determined from the electrodes 30 themselves by using, for example, voltages measured by the electrodes 30.

The visualization, navigation, and mapping subsystem 18 may utilize an electric field-based system, such as, for example, the ENSITE NAVX™ system commercially available from St. Jude Medical., Inc. and as generally shown with reference to U.S. Pat. No. 7,263,397 titled "Method and Apparatus for Catheter Navigation and Location and Mapping in the Heart," the entire disclosure of which is incorporated herein by reference, or the ENSITE VELOCITY™ system running a version of the NAVX™ software.

In other exemplary embodiments, the subsystem 18 may utilize systems other than electric field-based systems. For example, the subsystem 18 may comprise a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, the subsystem 18 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No. 7,386,339 entitled "Medical Imaging and Navigation System," the disclosures of which are incorporated herein by reference in their entireties.

In a further exemplary embodiment, the subsystem 18 may utilize a combination electric field-based and magnetic field-based system, such as, for example and without limitation, the CARTO 3™ system also commercially available from Biosense Webster, and as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the subsystem 18 may comprise or be used in conjunction with other commonly available systems, such as, for example and without limitation, fluoroscopic, computed tomography (CT), and magnetic resonance imaging (MRI)-based systems.

In an exemplary embodiment wherein the subsystem 18 comprises an electric field-based system, and as described above, the catheter 16 includes a plurality of electrodes 30 configured to both acquire EP data and produce signals indicative of catheter position and/or orientation information (positioning data). The subsystem 18 may use, for example and without limitation, time-division multiplexing or other similar techniques such that positioning data indicative of the position of the electrodes 30 is measured intermittently with EP data. Thus, an electric field used to locate the electrodes 30 may be activated between measurements of EP data, and the electrodes 30 may be configured to measure both EP data and the electric field from the subsystem 18, though at different times.

In other exemplary embodiments, however, wherein the electrodes 30 may not be configured to produce positioning data, the catheter 16 may include one or more positioning sensors in addition to the electrodes 30. In one such embodiment, the catheter 16 may include one or more positioning electrodes configured to generate signals indicative of the 3-D position or location of the positioning electrode(s). Using the position of the positioning electrode(s) along with a known configuration of the catheter 16 (e.g., the known spacing between the positioning electrode(s) and the electrodes 30) the position or location of each electrode 30 can be determined.

Alternatively, in another exemplary embodiment, rather than comprising an electric-field based system, the subsystem 18 comprises a magnetic field-based system. In such an embodiment, the catheter 16 may include one or more magnetic sensors (e.g., coils) configured to detect one or more characteristics of a low-strength magnetic field. The detected characteristics may be used, for example, to determine a 3-D position or location for the magnetic sensors(s), which may then be used with a known configuration of the catheter 16 to determine a position or location for each electrode 30.

For purposes of clarity and illustration only, the subsystem 18 will be described hereafter as comprising an electric field-based system, such as, for example, the ENSITE NAVX™ or VELOCITY™ systems identified above. Further, the description below will be limited to an embodiment of the system 10 wherein the electrodes 30 are configured to both acquire EP data and produce positioning data. It will be appreciated in view of the above, however, that the present disclosure is not meant to be limited to an embodiment wherein the subsystem 18 comprises an electric field-based system or the electrodes 30 serve a dual purpose or function. Accordingly, embodiments wherein the subsystem 18 is other than an electric field-based system, and the catheter 16 includes positioning sensors in addition to the electrodes 30 remain within the spirit and scope of the present disclosure.

With reference to FIGS. 1 and 6, in an exemplary embodiment the subsystem 18 may include an electronic control unit (ECU) 100 and a display device 102. Alternatively, one or both of the ECU 100 and the display device 102 may be separate and distinct from, but electrically connected to and configured for communication with, the subsystem 18. The subsystem 18 may still further include a plurality of patch electrodes 104, among other components. With the exception of a patch electrode 104$_B$ called a "belly patch," the patch electrodes 104 are provided to generate electrical signals used, for example, in determining the position and orientation of the catheter 16, and in the guidance thereof. The catheter 16 may be coupled to the ECU 100 or subsystem 18 with a wired or wireless connection. A wireless connection may involve Bluetooth, Wi-Fi, or any other wireless communication protocol, for example, and may be more flexible than a wired connection.

In one embodiment, the patch electrodes 104 are placed orthogonally on the surface of the body 14 and are used to create axes-specific electric fields within the body 14. For instance, patch electrodes 104$_{X1}$, 104$_{X2}$ may be placed along a first (x) axis. Patch electrodes 104$_{Y1}$, 104$_{Y2}$ may be placed along a second (y) axis, and patch electrodes 104$_{Z1}$, 104$_{Z2}$ may be placed along a third (z) axis. These patches may act as a pair or dipole. In addition or in the alternative, the patches may be paired off an axis or paired in series, e.g., 104$_{X1}$ is paired with 104$_{Y1}$, then 104$_{Y2}$, 104$_{Z1}$, 104$_{Z2}$. In addition, multiple patches may be placed on one axis, e.g., under the patient. Each of the patch electrodes 104 may be coupled to a multiplex switch 106. In an exemplary embodiment, the ECU 100 is configured, through appropriate software, to provide control signals to the switch 106 to thereby sequentially couple pairs of electrodes 104 to a signal generator 108. Excitation of each pair of electrodes 104 generates an electric field within the body 14 and within an area of interest such as the tissue 12. Voltage levels at the non-excited electrodes 104, which are referenced to the belly patch 104$_B$, are filtered and converted and provided to the ECU 100 for use as reference values.

With the electrodes 30 electrically coupled to the ECU 100, the electrodes 30 are placed within electrical fields that the patch electrodes 104 create in the body 14 (e.g., within the heart) when the patch electrodes 104 are excited. The electrodes 30 experience voltages that are dependent on the respective locations between the patch electrodes 104 and the respective positions of the electrodes 30 relative to the tissue 12. Voltage measurement comparisons made between the electrodes 30 and the patch electrodes 104 can be used to determine the position of each electrode 30 relative to the tissue 12. Accordingly, the ECU 100 is configured to determine position coordinates (x, y, z) of each electrode 30. Further, movement of the electrodes 30 near or against the tissue 12 (e.g., within a heart chamber) produces information regarding the geometry of the tissue 12.

The information relating to the geometry of the tissue 12 may be used, for example, to generate models and/or maps (as will be described in greater detail below) of anatomical structures that may be displayed on a display device, such as, for example, the display device 102. Information received from the electrodes 30 can also be used to display on the display device 102 the location and orientation of the electrodes 30 and/or the tip of catheter 16 relative to the tissue 12. Accordingly, among other things, the ECU 100 may provide a means for generating display signals for the display device 102 and for creating a graphical user interface (GUI) on the display device 102. It should be noted that in some instances where the present disclosure refers to objects as being displayed on the GUI or the display device 102, this may actually mean that representations of these objects are being displayed on the GUI or the display device 102.

It should also be noted that while in an exemplary embodiment the ECU 100 is configured to perform some or all of the functionality described above and below, in another exemplary embodiment, the ECU 100 may be separate and distinct from the subsystem 18, and the subsystem 18 may have another ECU configured to perform some or all of the functionality described herein. In such an embodiment, that ECU could be electrically coupled to, and configured for communication with, the ECU 100. However, for purposes of clarity and illustration only, the description below will be limited to an embodiment wherein the ECU 100 is shared between the subsystem 18 and the system 10 and is configured to perform the functionality described herein. Still further, despite reference to a "unit," the ECU 100 may comprise a number or even a considerable number of components (e.g., multiple units, multiple computers, etc.) for achieving the exemplary functions described herein.

In some embodiments, then, the present disclosure contemplates the ECU 100 as encompassing components that are in different locations.

The ECU 100 may include, for example, a programmable microprocessor or microcontroller, or may comprise an application specific integrated circuit (ASIC). The ECU 100 may include a central processing unit (CPU) and an input/output (I/O) interface through which the ECU 100 may receive a plurality of input signals including, for example, signals generated by the patch electrodes 104 and the positioning sensors 30. The ECU 100 may also generate a plurality of output signals including, for example, those used to control the display device 102 and the switch 106. The ECU 100 may be configured to perform various functions, such as those described in greater detail above and below, with appropriate programming instructions or code. Accordingly, in one embodiment, the ECU 100 is programmed with one or more computer programs encoded on a computer-readable storage medium 110 for performing the functionality described herein.

In addition to the above, the ECU 100 may further provide a means for controlling various components of the system 10 including, but not limited to, the switch 106. In operation, the ECU 100 generates signals to the control switch 106 to thereby selectively energize the patch electrodes 104. The ECU 100 receives positioning data from the catheter 16 reflecting changes in voltage levels and from the non-energized patch electrodes 104. The ECU 100 uses the raw positioning data produced by the patch electrodes 104 and the electrodes 30, and corrects the data to account for respiration, cardiac activity, and other artifacts using known or hereinafter developed techniques. The corrected data, which comprises position coordinates corresponding to each of the electrodes 30 (e.g., (x, y, z)), may then be used by the ECU 100 in a number of ways, such as, for example and without limitation, to create a geometrical anatomical model of an anatomical structure or to create a representation of the catheter 16 that may be superimposed on a map, model, or image of the tissue 12 generated or acquired by the ECU 100.

Figure 7:
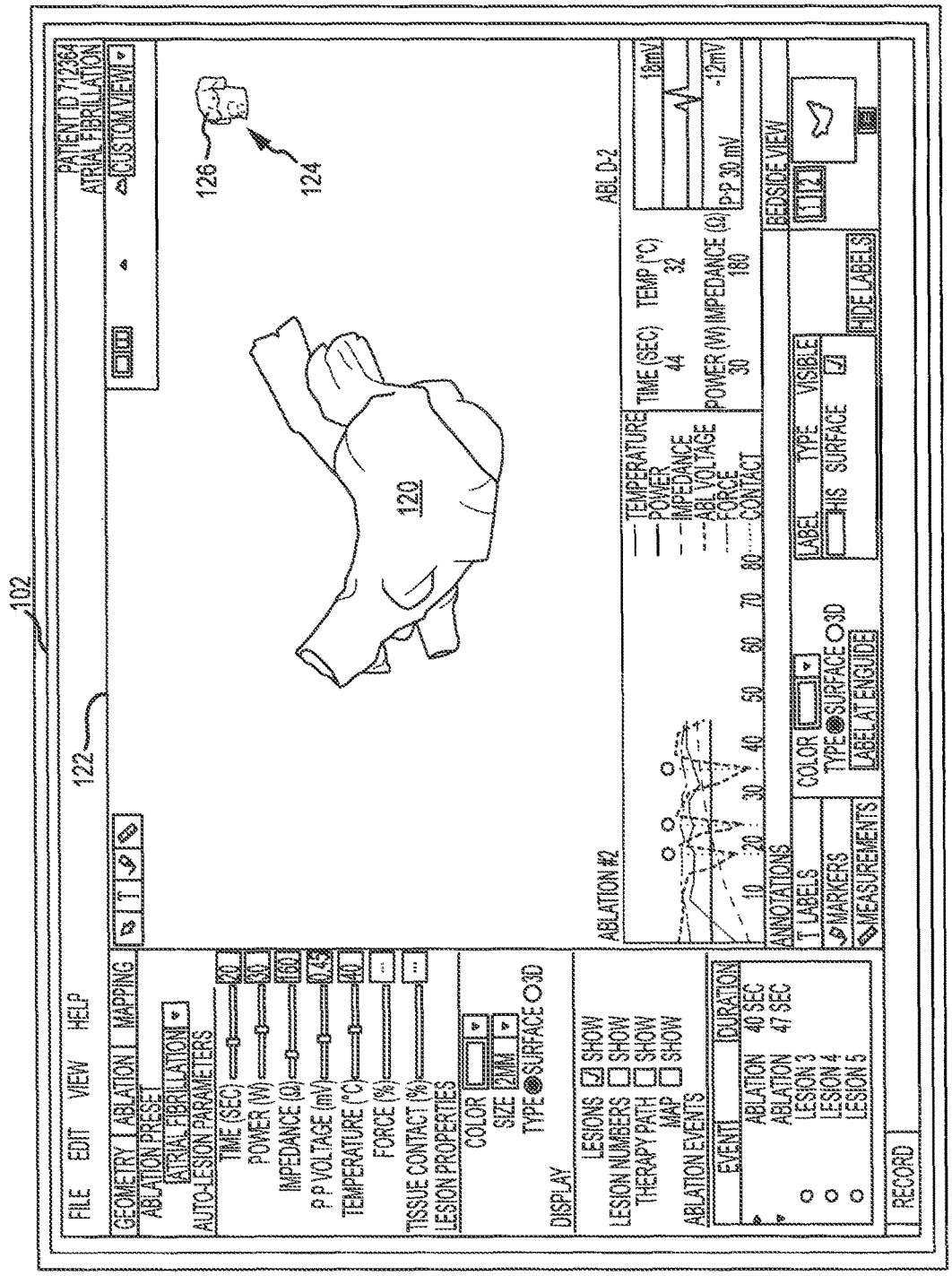
FIG. 7 is a representation of an exemplary embodiment of a display device of the system illustrated in FIG. 1 with a graphical user interface (GUI) displayed thereon.

The ECU 100 may be configured to construct a geometrical anatomical model 120 of the tissue 12 for display on the display device 102, as shown in FIG. 7. The ECU 100 may also be configured to generate a GUI 122 through which a user may, among other things, view the geometrical anatomical model 120. The ECU 100 may use positioning data acquired from the electrodes 30 or other sensors on the distal end 28 or from another catheter to construct the geometrical anatomical model 120. In one embodiment, positioning data in the form of a collection of data points may be acquired from surfaces of the tissue 12 by sweeping the distal end 28 of the catheter 16 along the surfaces of the tissue 12. From this collection of data points, the ECU 100 may construct the geometrical anatomical model 120. One way of constructing the geometrical anatomical model 120 is described in U.S. patent application Ser. No. 12/347,216 entitled "Multiple Shell Construction to Emulate Chamber Contraction with a Mapping System," the entire disclosure of which is incorporated herein by reference. Moreover, the anatomical model 120 may comprise a 3-D model or a two-dimensional (2-D) model. As will be described in greater detail below, a variety of information may be displayed on the display device 102, and in the GUI 122 displayed thereon, in particular, in conjunction with the geometrical anatomical model 120, such as, for example, EP data, images of the catheter 16 and/or the electrodes 30, metric values based on EP data, HD surface maps, and HD composite surface maps.

To display the data and images that are produced by the ECU 100, the display device 102 may comprise one or more conventional computer monitors other display devices well known in the art. It is desirable for the display device 102 to use hardware that avoids aliasing. To avoid aliasing, the rate at which the display device 102 is refreshed should be at least as fast as the frequency with which the ECU 100 is able to continuously compute various visual aids, such as, for example, HD surface maps.

As illustrated in FIG. 7, in an exemplary embodiment, the ECU 100 may generate a worldview upper torso 124 on the display device 102. The worldview upper torso 124, which may be fully rotatable, may serve to inform or remind the viewer of the perspective in which the heart is being viewed, accessed, or manipulated—and hence where the distal end 28 is located. For example, the worldview upper torso 124 may help the viewer identify the right ventricle from the left ventricle based on whether a chest 126 or a back of the worldview upper torso 124 is shown. Other, similar icons may be used to the same purpose.

As described above, the plurality of electrodes 30 disposed at the distal end 28 of the catheter 16 are configured to acquire EP data. The data collected by the respective electrodes 30 may be collected simultaneously. In one embodiment, EP data may comprise at least one electrogram. An electrogram indicates the voltage measured at a location (e.g., a point along tissue 12) over a period of time. By placing a high density of electrodes 30 on the distal end 28, the ECU 100 may acquire a set of electrograms measured from adjacent locations in the tissue 12 during the same time period. The adjacent electrode 30 locations on the distal end 28 may collectively be referred to as a "region."

The ECU 100 may also acquire times at which electrograms are measured, the positions from which electrograms are measured, and the distances between the electrodes 30. As for timing data, the ECU 100 may track, maintain, or associate timing data with the voltages of each electrode 30 as measured. In addition, the 3-D position coordinates of each electrode 30 as it measures voltages may be determined, for example, as described above by the visualization, navigation, and mapping subsystem 18. The ECU 100 may be configured to continuously acquire position coordinates of the electrodes 30, especially when the electrodes 30 are measuring EP data. Because the ECU 100 may know the spatial distribution of electrodes 30 of each distal end 28 configuration (e.g., matrix-like, spiral, basket, etc.), the ECU 100 may recognize from the position coordinates of the electrodes 30 which configuration of the distal end 28 is deployed within a patient. Furthermore, the distances between the electrodes 30 may be known by the ECU 100 because the electrodes 30 may be precisely and strategically arranged in a known spatial configuration. Thus, if the distal end 28 is not deformed, a variety of analyses may use the known distances between the electrodes 30 without having to obtain the coordinate positions from the subsystem 18 to solve for the distances between the electrodes 30.

With the ECU 100 having voltage, timing, and position data corresponding to the respective electrodes 30 in addition to the known electrode 30 spatial configuration, many comparative temporal and spatial analyses may be performed, as described below. Some of these analyses lead to creation of HD surface maps representing activation patterns from the tissue 12, which are possible in part because of the high density of the electrodes 30 at the distal end 28 of the shaft 24. By providing a high density of electrodes at the distal end 28, the accuracy and resolution of HD surface maps produced by the system 10 are enhanced.

Moreover, one particularly beneficial aspect of the distal end 28 having a high density of electrodes 30 is the robust nature in which it measures EP data suitable for bipolar comparisons by the ECU 100. Bipolar comparisons indicate the difference in voltage between two spaced-apart poles (i.e., electrodes 30) at a given point in time. However, not all bipolar arrangements capture all depolarization waves that traverse the tissue 12. For example, if a depolarization wave that is parallel to a pair of electrodes 30 that are spaced apart across the distal end 28 approaches and passes the pair of electrodes 30 at the same time, a bipolar comparison of the pair of the electrodes 30 will not indicate any difference in voltage due to the parallel depolarization wave. With a high density of electrodes, though, a wave that is parallel to one pair of electrodes 30 (i.e., two poles or bipoles of a bipolar arrangement) may not necessarily be parallel to other pairs of electrodes 30 (i.e., two poles or bipoles of a bipolar arrangement) on the distal end 28. Therefore, the distal end 28 provides a more robust way of comparing bipolar EP data because a high density of electrodes 30 captures a wider variety of wavefront patterns.

In one embodiment, bipolar comparisons may be made from pairs of electrodes 30 along the distal end 28 where the pairs are angularly spaced apart from one another. Having angularly spaced-apart electrode pairs on the distal end 28 readily provides for a determination of wavefront direction regardless of an orientation of the distal end 28. Wavefront direction and other determinations are possible because the spatial distribution of sensors may be used to compute optimal bipolar electrograms. For example, each sensor may be paired with all of its neighboring sensors, and then the ECU 100 may adaptively select the most negative bipolar electrogram. The neighborhood may be defined based on either the catheter model in the static fashion or with ENSITE NAVX™ impedances in the dynamic fashion. The optimal bipolar electrogram includes the traditional bipolar electrogram by definition, so the optimal bipolar electrogram may provide even more diagnostic information. Optimal bipolar EP data subject to predefined functions (e.g., most negative, most positive) can be more sensitive to a change in the electric field. Thus, this enhanced EP signal may facilitate even better cardiac activation detection.

Another advantage of having a high density of electrodes 30 at the distal end 28 is that concentrated arrhythmias, and/or associated symptoms, side effects, or indications thereof, are more likely to be detected. For example, short radius entry depolarization wavefront patterns, which are relatively small when compared to other depolarization wavefront patterns, may go unnoticed by traditional catheters or even catheters having multiple electrodes that are spaced, relatively speaking, too far apart. On the other hand, by taking into consideration the magnitude of even the smallest depolarization wavefront patterns, the electrodes 30 at the distal end 28 may be spatially distributed to measure even the smallest depolarization wavefront patterns.

With respect to capturing or collecting EP data measured by the high density of electrodes 30, in one embodiment, the ECU 100 may be programmed to continuously record and analyze data in real-time or near real-time. In another embodiment, a user may specify through a user input device a time window (e.g., 200 ms, 20 seconds, etc.) during which the ECU 100 may capture data measured from the electrodes 30. The user input device may include, for example and without limitation, a mouse, a keyboard, a touch screen, and/or the like. It should be noted that in one embodiment, the electrodes 30 may continuously measure voltages along the tissue 12, and the ECU 100 may selectively capture or record such voltages from the electrodes 30. In still another embodiment, the electrodes 30 measure voltages in accordance with a sampling rate or command from the ECU 100. Once the distal end 28 of the shaft 24 is positioned near or along the tissue 12 as desired, the user could prompt a trigger for the time window. The user may configure the trigger for the time window to correspond, for example, to a particular cardiac signal or the expiration of a timer. To illustrate, the trigger could be set so the ECU 100 records data from the electrodes 30 before, during, and after an arrhythmia breakout or disappearance. One possible way to capture the data occurring just prior to the particular cardiac signal would be to use a data buffer that stores data (which may later be obtained) for an amount of time.

As noted above, the ECU 100 may be configured to recognize particular cardiac signals to trigger the time window. To that end, the electrodes 30 may constantly measure EP data when positioned near the tissue 12. This may be the case even if the user has not prompted the trigger for the time window. For example, the ECU 100 may recognize that the distal end 28 is near tissue 12 inside the body 14 based on the continuous measurements in the range of voltages that are expected near the tissue 12. Or the ECU 100 may, for example, be configured to constantly monitor voltages from the electrodes 30 when the ECU 100 is powered "on." In any event, the ECU 100 may continuously acquire EP data and continuously assess patterns and characteristics in the EP data. For example, the ECU 100 may be programmed to continuously apply a matched filter on electrograms recorded from certain predetermined electrodes 30 (e.g., the electrodes 30 that are adjacent to each other).

To detect the presence of waveform patterns known to be associated with certain arrhythmias, the matched filter may be used to compare a number of these known waveform patterns with the waveforms of the electrograms acquired by the electrodes 30. For example, based on prior experience, the peak-to-peak (PP) voltages associated with a particular arrhythmia may be known. Even before the user prompts the system 10 to record data, the ECU 100 may compare the PP voltages of the particular arrhythmia with the electrograms from the electrodes 30. Once the user prompts the system 10, the ECU 100 may record EP data from the electrodes 30 for the specified time window when the ECU 100 next "sees" the known waveform pattern.

In one exemplary embodiment, as EP data is acquired, or after EP data is acquired, an assortment of analog or digital signal processing and conditioning instrumentation for equalizing, filtering, or generally enhancing the characteristics of the acquired raw data, may be used. In some instances, it may be desirable for the system 10 to calculate various gradient metrics, as discussed below. Gradients, though, are inherently noisy and demand densely sampled and clean data. While the high density of electrodes 30 disposed on the distal end 28 help in obtaining gradients, oftentimes raw data signals need refining.

By equalizing data signals, and in particular certain phases of data signals, subsequent signal processing steps may become more robust. One such equalization, for example, may be appropriate where a reliable, large amplitude signal originates from a repetitive reentrant arrhythmia that repeats a circuit around some part of the tissue 12. In the case of arrhythmia breakout, for example, the time interval of interest may immediately precede the breakout. Therefore, empiric or adaptive adjustments may be made with respect to that particular time interval. As a further example, in the case of arrhythmia disappearance, the time interval of interest may immediately follow the disappearance. Likewise, analogous adjustments may be made.

Weak activation data in electrograms may also need to be amplified. In one embodiment, electrogram signal gain may be altered with time to emphasize weak signals. In another embodiment, electrogram signal conditioning may vary with time to help emphasize rapid changes in amplitude, whether increases or decreases. Doing so may homogenize signal strength for a more reliable determination of activation timing. In one embodiment, this may be accomplished by applying a multiplier-like operation. Moreover, additional high pass filtering may be applied at the time when the signal is most likely to grow or diminish using a state variable filter.

To further enhance the output that the system 10 and/or the ECU 100 generate, a user, the system 10, and/or the subsystem 18 may characterize certain locations of the tissue 12 as represented by the geometrical anatomical model 120. Once the anatomical model 120 is either created or acquired by the visualization, navigation, and mapping subsystem 18, certain locations may be flagged that are typically prone to, or have been identified in the past as, fostering arrhythmias (hereinafter "areas of interest"). Characterizing areas of interest in tissue 12 may not necessarily be automated, although the system 10 or the subsystem 18 may recognize some structural features of the tissue 12 typically associated with certain electrical conductive characteristics.

Depending on skill level, the user may recognize and use the user input device to mark particular locations having certain anatomical characteristics known to affect functional characteristics (e.g., electrical conductivity). For example, the user may identify locations known to constrain conduction, locations known to foster low depolarization amplitudes, locations known to exhibit particular conduction paths, or locations known to foster low conduction velocities. These locations may feature certain anatomical characteristics such as, for example, certain wall thicknesses, anatomical bundles, scars, smoothness, muscularity, and openings. To illustrate, the user may mark a ridge or a junction where a vein and an appendage come together to form a common part of the heart wall. Imaging modalities such as computed tomography (CT), magnetic resonance imaging (MRI), and ultrasound, for example, can also be used to identify such locations and/or anatomical characteristics.

If this information is provided, the system 10 may utilize this information advantageously in the steps ahead. For example, the ECU 100 may generate a cardiac anatomy metric based on this information and then later prompt a user to acquire more-than-usual amounts of EP data at these locations. Also, the ECU 100 may consider these cardiac anatomy metrics when computing various metrics such as a consistency metric, for example, from EP data acquired from these areas of potential interest.

Figure 8A:
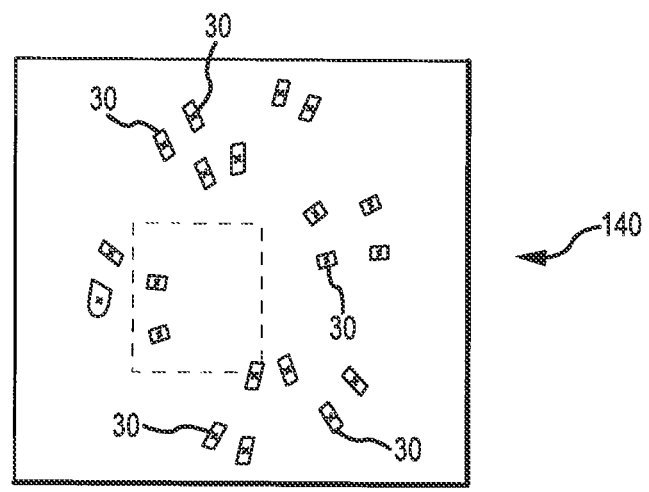
FIG. 8*a* is a schematic representation of positioning coordinates of sensors mounted on a medical device having a distal end arranged in a spiral configuration.
Figure 8B:
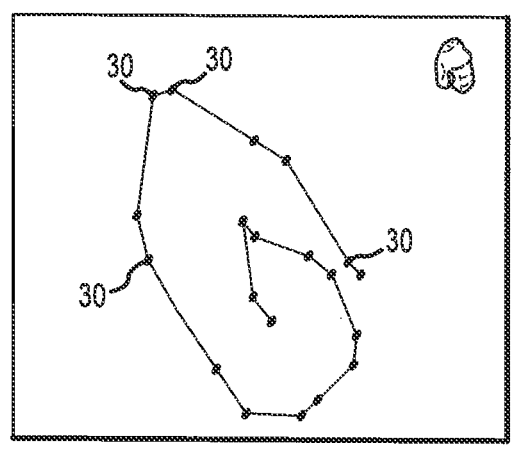
FIG. 8*b* is a schematic representation of raw positioning data corresponding to sensors mounted on a medical device having a distal end arranged in a spiral configuration, wherein the raw positioning data includes one or more inaccuracies that portray a distorted spatial arrangement of sensors of the medical device.

In some embodiments, after tissue 12 characterizations, EP data, positioning data, and/or other forms of input have been collected, an HD surface model may be constructed for registration to a geometrical anatomical model 120. The known spatial configuration of electrodes 30 may be used, as shown in FIG. 8a, as a model 140 to correct for any inaccuracies in raw measured data. In the example shown in FIG. 8a, the electrodes 30, and therefore the distal end 28 of the catheter 16, are known to be arranged in the spiral configuration. However, FIG. 8b shows position coordinates as computed by the subsystem 18 from raw measured data. Thus, because the distal end 28 is known not to be deformed as portrayed by the distorted positioning coordinates in FIG. 8b, inaccuracies in the raw measured data likely exist.

Figure 8C:
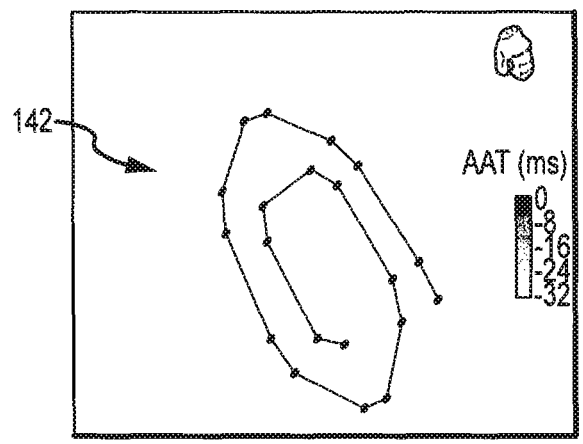
FIG. 8*c* is a schematic representation of corrected positioning coordinates corresponding to the raw positioning coordinates illustrated in FIG. 8*b*.
Figure 8D:
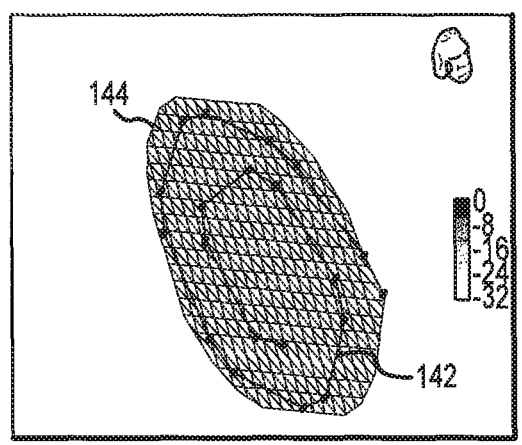
FIG. 8*d* is a schematic representation of a high density grid corresponding to the corrected positioning coordinates illustrated in FIG. 8*c*.

The ECU 100 may apply a correction algorithm to obtain corrected position coordinates based on the known coordinates from the model 140 shown in FIG. 8a and/or the measured position coordinates shown in FIG. 8b. One example of a correction algorithm is a least squares fitting algorithm, which may result in a corrected 3-D affine transformation set of data 142, as represented in FIG. 8c. EP data values measured with the electrodes 30 may also be correlated to the corrected position coordinates. Next, FIG. 8d shows how the ECU 100 may interpolate the affine transformation data set 142 to obtain an HD grid 144. The ECU 100 may interpolate both the corrected position coordinates of the affine transformation data set 142 and the EP data values associated with each corrected position coordinate. As interpolated, the HD grid 144 provides a more refined set of data points with which to use in computing metric values and displaying surface maps and composite maps, etc.

Data from the fitting process provides additional information to verify sensor positions calculated from EP data. If the data is above a predefined tolerance, the measured coordinates are considered unreliable and thus corrected coordinates should not be used for the following data analysis. The fitting algorithm can also be used to detect if the distal end of the catheter has mechanical deformation. For example, an inner loop and an outer loop of the spiral configuration may be designed for alignment along a 2D plane. The distribution of sensors on the inner loop may be registered with the distribution of sensors on the outer loop using the fitting algorithm. If a normal of the 2D plane constrained by the inner loop is significantly different from its counterpart of the outer loop, the catheter may be deformed.

The ECU 100 may use the HD grid 144 in creating HD surface maps that are viewable on the display device 102. With an even higher density of data points, even greater resolution HD surface maps are possible. The interpolated data points on either the HD grid 144 or an HD surface map may be referred to as "vertices."

One aspect of creating HD surface maps involves the ECU 100 using the corrected and interpolated position coordinates. Another aspect involves ECU 100 using the interpolated EP data values associated with the interpolated position coordinates. The ECU 100 may use the vertices from the HD grid 144 to associate the HD grid 144 to the known shape and points on the geometrical anatomical model 120. Associating may include, for example and without limitation, registering, fitting, matching, or otherwise superimposing. Once the HD grid 144 is associated with the geometrical anatomical model 120 and various EP data or resultant computed metric values thereof are displayed in the form of a map, as described below, the HD grid 144 may be more properly referred to as an HD surface map. The content of the HD surface map may depend on the interests of a user. Also, HD surface maps may be recomputed continuously, or at least as fast as the ECU 100 will allow.

In an alternative embodiment, the HD grid 144 and HD surface maps may be constructed without the prior construction of the geometrical anatomical model 120. In other words, the geometrical anatomical model 120 or portions thereof may essentially be constructed concurrently with the HD grid 144 and HD surface maps.

HD surface maps may reflect, among other things, the differences in the values or properties being represented at different locations on the map. One exemplary way in which the map may reflect these differences is by color coding. For example, the ECU 100 may be configured with a color scheme that considers the range of resultant values from a computed metric. Depending on the range of computed metric values, the ECU 100 may be configured to assign each value or sub-range of values an appropriate color (e.g., purple to white). In the alternative, the user could determine the range and/or scale of values that should be displayed in color. The color scheme could help highlight the range of values across the map, whether from one metric or numerous metrics. Moreover, color coding portions of the HD surface map may communicate spatial variation of specific properties. Some of these specific properties may include, for example, the resultant values of the metrics described below, raw EP data, etc. Yet further, color coded maps may be continuously updated such that the maps are dynamic and based on recently or the most-recently measured EP data or derivations thereof.

As for the content of the HD surface maps, the ECU 100 may be configured to compute one or more metrics, derivation metrics, and combination metrics (generally "metrics") and to display the values of those metrics on the HD surface maps or HD "composite" surface maps. Metrics are generally various quantifications of EP data, and maps of resultant metric values spatially depict these quantifications. In addition, metrics may refer to the quantification of EP data acquired from one or more electrodes 30.

Certain metrics based on EP data are well known in the art. These include, for example, local activation time (LAT), depolarization amplitude voltage (e.g., peak-to-peak amplitude (PP)), complex fractionated electrogram (CFE) activity, dominant frequency (DF), and Fast Fourier Transform (FFT) ratio. An LAT metric represents the difference in time between when a stationary reference electrode experiences a depolarization wavefront and when one or more roving electrodes (electrodes that are swept over or around the tissue 12) experience the depolarization wavefront. A PP metric represents an amount of change between the highest peak voltage and the lowest trough voltage experienced by a specific point on the tissue 12 during a depolarization wave. A CFE metric is described in U.S. Pat. No. 8,038,625 titled "System and Method for Three-Dimensional Mapping of Electrophysiology Information," the entire disclosure of which is incorporated herein by reference. A DF metric represents the most dominant frequency in a power spectrum analysis of a given interval of cardiac signal.

As described above, the system 10 is particularly efficient in obtaining EP data for these and other metrics because of the high density of electrodes 30 that can simultaneously measure EP data. Moreover, because the electrodes 30 of the distal end 28 can simultaneously measure EP data from the tissue 12, the system 10 does not have to time align signals measured from different locations at different points in time. Because of this, the system 10 provides significant temporal and spatial capabilities. Further, because of these capabilities, the ECU 100 may use metrics that are known in the art and/or the metrics described below to derive more-advanced metrics, to combine metrics, and/or to analyze complex arrhythmias.

In an exemplary embodiment, the ECU 100 may be configured to calculate values for additional metrics based at least in part on EP data collected by the electrodes 30. These metrics may include, for example and without limitation, an absolute activation time (AAT), a percentage fractionation index (PFI), a continuous spatial index (CSI), a conduction velocity vector, spatial gradients of depolarization amplitude, consistency metrics, and metrics based on a combination of two or more metrics, to name a few. Each of these metrics will be described in turn below. Although the following metrics may be described with reference to the electrodes 30 on the distal end 28, the ECU 100 can perform the same computations between vertices of the HD grid 144 after EP data and position coordinates have been interpolated.

Before proceeding with a description of these exemplary metrics, several terms should be explained in more detail. Variations of the term "depolarization" may have a range of meanings. In some exemplary embodiments, locations in the tissue 12 where the electrodes 30 are stationed (and where electrograms associated with the electrodes 30 are acquired) may be said to be "depolarizing" as the depolarization wave is passing. After the wave passes, these locations in the tissue 12 and the electrodes 30 may be said to have been "depolarized" or "activated."

Figure 9:
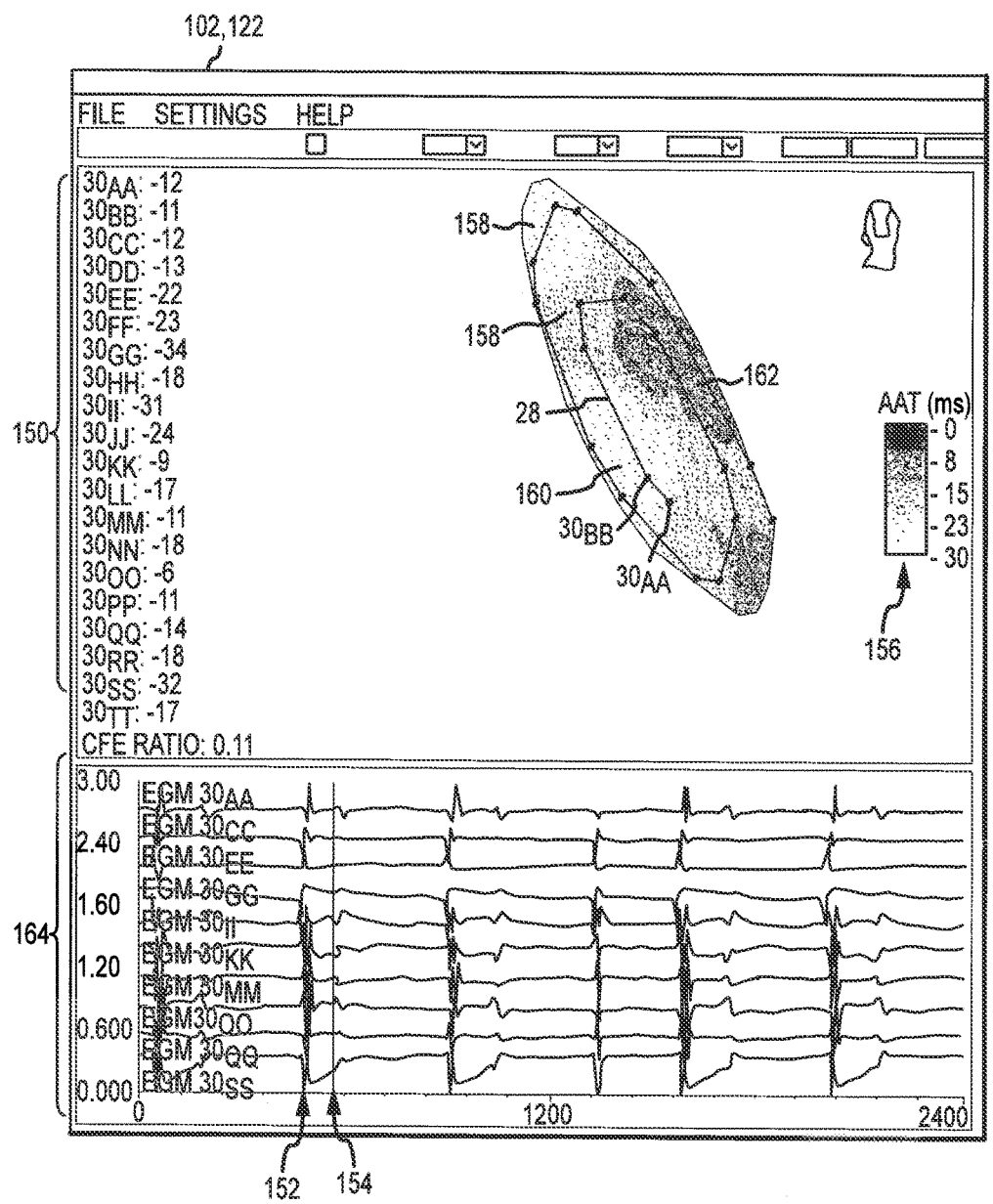
FIG. 9 is an exemplary representation of electrograms and a dynamic map illustrating an absolute activation time (AAT) metric in graphical form that may be displayed on a display device of the system illustrated in FIG. 1.

With reference to FIG. 9, the AAT metric will be described. A value of the AAT metric is calculated for one or more of the electrodes 30, as shown collectively by elapsed times 150. AAT values are indicative of an amount of time that has elapsed since a most recent activation at each electrode 30. Depolarization waves "activate" or "depolarize" different electrodes 30 (positioned at locations along the tissue 12) at different times. In other words, the AAT value for a particular electrode indicates the amount of time that has elapsed since a most-recent depolarization wave passed the particular electrode. A group of depolarizations occurring around a point in time 152 are shown for a plurality of electrodes in the electrogram waves illustrated in FIG. 9. The elapsed times 150 may be measured with reference to a position of an automated cursor 154 on the GUI 122 or, more generally, on the display device 102. The position of the cursor 154 corresponds to a point in time. In an alternative embodiment, the position of cursor 154 is not automated. A user may select the cursor 154 on the GUI 122 and move it in relation to the electrograms. Moving the cursor 154 to the left would correspond to an earlier point in time, while moving the cursor 154 to the right would correspond to a later point in time. Depending on the position of the cursor 154, the AAT metric value for each electrode 30 will change along with a corresponding spatial map of these values.

The dynamic map shown in FIG. 9 illustrates AAT computed for each bipolar electrogram captured from the electrodes 30 at the distal end 28. In this embodiment, the distal end 28 is in the spiral configuration and has twenty electrodes 30, each of which has its own AAT, though only ten of the corresponding electrogram waves are shown. The AATs for the twenty electrodes 30 are shown in the elapsed times 150. Each electrode 30 may have an identifier, such as "$30_{AA}$," for example, which distinguishes it from the other nineteen electrodes 30 disposed on the distal end 28 in this embodiment. Based on the elapsed times 150 shown, the electrode $30_{OO}$ has an AAT of (−6) milliseconds. The electrode $30_{GG}$ has an AAT of (−34) milliseconds. Thus, a depolarization wave passed the electrode $30_{OO}$ six milliseconds prior to a point in time corresponding to the position of the cursor 154. And a depolarization wave passed the electrode $30_{GG}$ thirty-four milliseconds prior to the same point in time corresponding to the position of the cursor 154.

Unlike conventional maps such as LAT and PP maps, the dynamic AAT map may allow a user to identify and analyze multiple depolarization wavefronts evident in certain arrhythmias. The dynamic AAT map in FIG. 9 may be color coded with a legend 156 to indicate the times elapsed from activation, with each color region 158 corresponding to a different range of times. One of ordinary skill in the art will recognize a relatively planar wavefront from a left part 160 of the map display to a right part 162. Specifically, the left part 160 of the map shows activation times in the range of minus 20-30 milliseconds while the right part 162 of the map shows activation times in the range of minus 0-10 milliseconds.

Further, as described above, the cursor 154 may represent the current time of interest, whether determined by a user or automatically by the ECU 100. As the cursor 154 changes positions, the coloring of the map may change indicating cardiac wavefront direction. From the perspective of each electrode 30, when a depolarization wave from any source passes, the AAT for each respective electrode 30 may reset to zero. Thus, with normal EP wavefront activity, the AAT values of the electrodes 30 may reset in a relatively orderly progression. In a state of arrhythmia, however, the resetting of AAT values associated with the electrodes 30 may not be orderly.

Another metric for which the ECU 100 may calculate a value is the percentage fractionation index, or PFI. The PFI may represent the relative amount of time that an electrogram, which may be acquired by a single electrode at a single site, spends depolarizing during a timeframe. In one embodiment, the ECU 100 may determine a timeframe of interest. For example, the ECU 100 may begin to capture EP data from the electrodes 30 when electrical voltages measured from the tissue 12 exhibit characteristics of arrhythmia. In another embodiment, a user can specify the timeframe. PFI can be described with reference to the electrograms displayed in a lower viewing pane 164. Taking again the electrogram labeled "EGM $30_{GG}$" corresponding to the electrode $30_{GG}$, for example, a PFI could be calculated based on the amount of time that this electrogram spends depolarizing during the timeframe of interest. Here, the timeframe is shown to be 2000 milliseconds, because the units along the X-axis are number of 1200 Hz samples, where 1200 Hz is equivalent to 1000 milliseconds and 2400 Hz is equivalent to 2000 milliseconds. The electrogram EGM $30_{GG}$ experiences six depolarizations, one of which is shown near the time 152, during this timeframe. If it is assumed that each depolarization occurs over a 60 millisecond interval, the electrogram will spend 360 milliseconds depolarizing during this 2000 millisecond timeframe. PFI may be represented as a percentage or in milliseconds. Thus, the PFI for this electrogram during the timeframe may be represented as 360 milliseconds or, in the alternative, eighteen percent of the overall evaluation timeframe.

The PFI value for a piece of tissue 12 becomes particularly helpful when compared to the PFI values of other electrograms. The ECU 100 or a user may compare the measured and computed PFI value, for example, with PFI values computed from other electrograms measured from the tissue 12, with PFI values measured from locations on the tissue 12 where no state of arrhythmia is present, or with PFI values measured from tissue in a healthy state. In short, areas of interest on the tissue 12 are likely to experience more depolarization wavefronts than are healthy areas on tissue 12. Areas of interest on the tissue 12, therefore, are also likely to spend a larger percentage of time depolarizing than locations that do not accommodate arrhythmias. Thus, the higher the PFI value, the more likely it is that the location from which that PFI value was computed is experiencing an arrhythmia.

Hence, if the PFI value for healthy heart tissue is much lower than twenty percent, this may indicate that the location from which electrogram EGM $30_{GG}$ was calculated is an area of interest. On average, healthy tissue may spend 60 milliseconds depolarizing per heartbeat, and on average, healthy tissue may experience 80 heart beats per minute. This would suggest that healthy tissue spends about 160 milliseconds $$\left( \frac{80 hb}{1 \text{ min}} \times \frac{1 \text{ min}}{60000 \text{ ms}} \times (2000 \text{ ms}) \times (60 \text{ ms}) \right)$$

depolarizing during a 2000 millisecond window. In this example with the EGM $30_{GG}$, then, it is likely that the electrogram EGM $30_{GG}$ was measured from an area of interest since it spends almost double the normal amount of time depolarizing. A user may control, for a variety of purposes, default values such as how long healthy tissue spends depolarizing, healthy PFI values, etc.

Yet another metric that the ECU 100 may compute is the continuous spatial index, or CSI. The CSI, which is similar to the PFI, is the summation of the amount of time that at least one electrogram of a set spends depolarizing during a time window. In one exemplary embodiment, a set may be defined by electrograms acquired from the electrodes 30 disposed along the distal end 28 of the catheter 16. In other embodiments, a set may include some other combination of electrograms. For example, a set may include electrograms measured from positioning the distal end 28 along several adjacent locations on the tissue 12, particularly if these locations are suspected areas of interest. As a further example, the set may comprise only some of the electrograms measured from the distal end 28. In still other embodiments, the set may comprise one or more electrodes from numerous catheters.

The CSI metric may be particularly helpful in identifying certain types of wavefront patterns, which are described below. For example, a set of electrograms experiencing normal, planar depolarization wavefronts will have a relatively low CSI percentage value. This may be true especially where the electrodes 30 measuring the electrograms are aligned such that numerous electrodes 30 experience the depolarization wave at roughly the same time. But on the other hand, at least one electrogram (or electrode) from a set of electrograms that is experiencing a generally circular wavefront pattern will be constantly depolarizing. Thus, this latter set of electrograms may have a CSI value near 100 percent. Therefore, like PFI, a high CSI value suggests an area of interest.

The ECU 100 may also compute a conduction velocity metric. The values of this metric may be mapped to show 2-D vectors representing the direction and conduction velocity of underlying depolarization wavefronts in the tissue 12. Each electrode 30 could have a depolarization wavefront velocity direction and speed computed and displayed, if desired. Moreover, the ECU 100 may be configured in one embodiment to generate a map of the conduction velocity metric as soon as the distal end 28 is positioned sufficiently close to the tissue 12. To determine the proximity of the distal end 28 to the tissue 12, the ECU 100 may utilize, for example, ENSITE CONTACT™ technology and Euclidean distance between the electrodes 30 and a geometrical anatomical model, such as model 120 of FIG. 7.

Figure 10A:
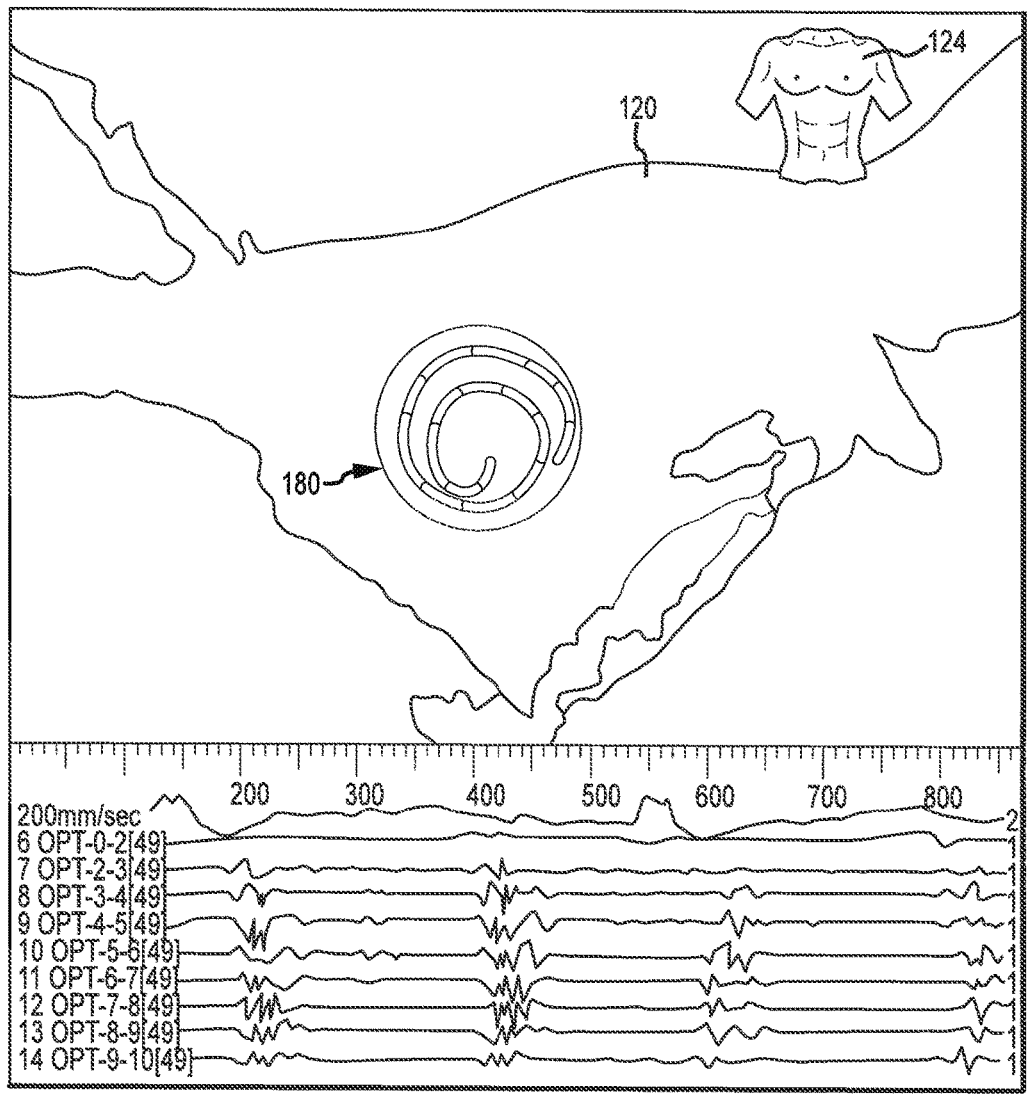
FIG. 10a is an exemplary representation of electrograms and a map depicting a representation of a distal end of a medical device approaching tissue to be measured that may be displayed on a display device of the system illustrated in FIG. 1.
Figure 10B:
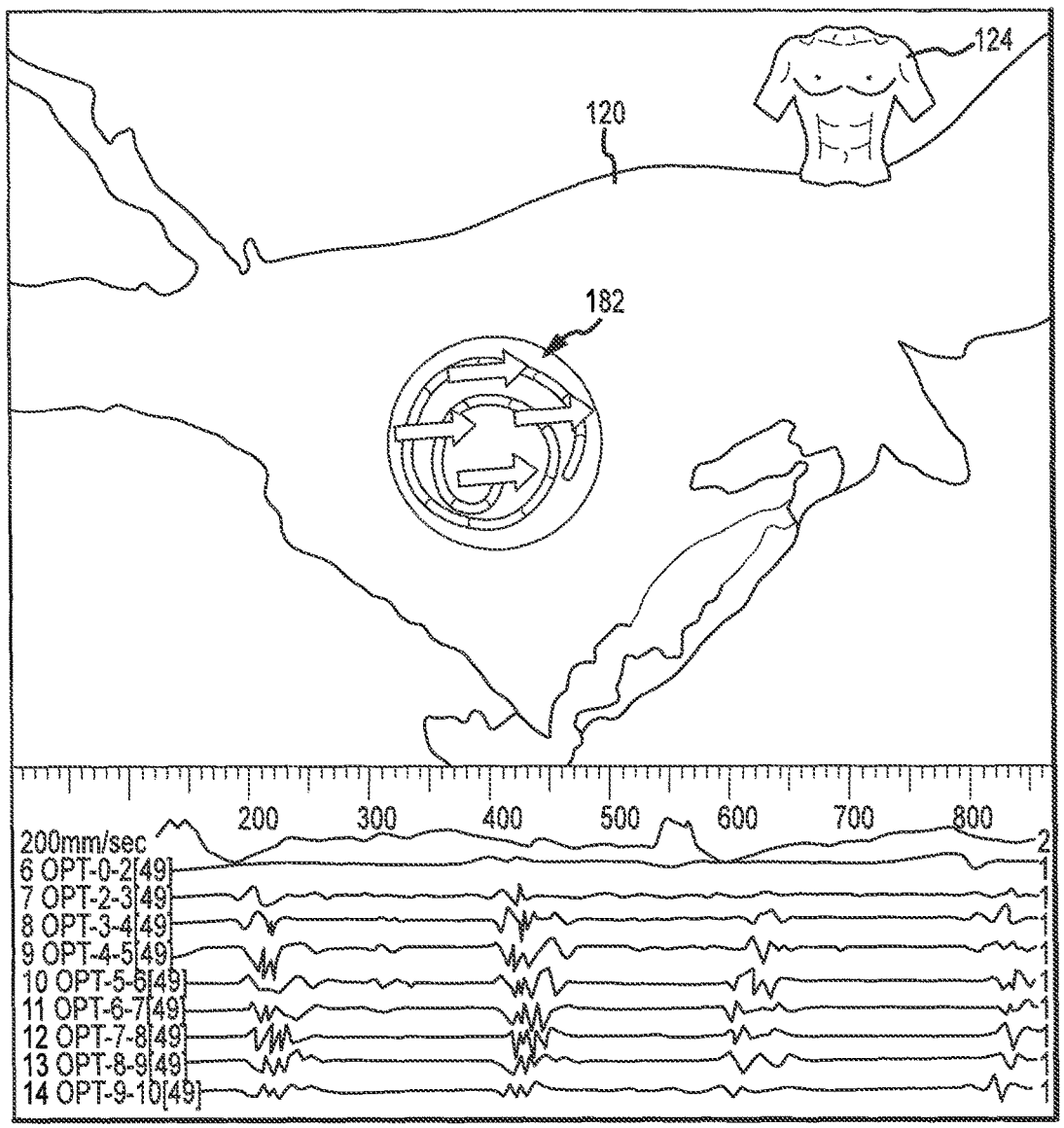
FIG. 10b is an exemplary representation of electrograms and a map depicting a conduction velocity metric, which shows cardiac direction and speed, with respect to an associated geometrical anatomical model.

However, when the distal end 28 is not sufficiently close to the tissue 12, the ECU 100 may prevent the display of the conduction velocity metric values because the electrodes 30 may not be in a position to acquire quality EP data or a sufficient amount of quality EP data. FIG. 10a shows a representation 180 of the distal end 28 without any conduction velocity vectors. The representation 180 may be displayed when the distal end 28 approaches the tissue 12, but is too remote to measure quality data. As the distal end 28 is moved closer to the tissue 12, resultant values from the conduction velocity metric may be spatially mapped on the geometrical anatomical model 120 in the form of an HD surface map 182, as shown in FIG. 10b. More particularly, indicators representative of the velocity and direction of the wavefront may be superimposed onto the geometrical anatomical model 120, as described below. Precluding updates or the display of conduction velocity vectors until the distal end 28 is sufficiently close to the tissue 12 is just one of many measures of quality control throughout the system 10.

In any event, the ECU 100 may use the coordinate positions of the electrodes 30 and the times at which depolarization waves pass the electrodes 30 to compute the conduction velocity metric. In the case that the distal end 28 is not deformed, the ECU 100 would not need the coordinate positions of the electrodes 30 to compute conduction velocity and may instead use the known distances between the electrodes 30 arranged in the known spatial configuration. The times at which peaks of depolarization waves pass the electrodes 30 may be determined from corresponding electrograms by employing signal processing techniques known in the art.

The system 10 can determine the direction at which a wavefront passes a specific electrode 30 on the distal end 28 by comparing activation times of neighboring electrodes 30. The result of this determination, if mapped, would appear like arrows 184 on a top right rendering window 186 shown in FIG. 11. This capability of the system 10 is attributable, at least in part, to the high spatial density of electrograms acquired by the ECU 100.

For example, the activation time of an electrode 30 that is positioned centrally to five surrounding electrodes 30 may be compared to the activation times of the five surrounding electrodes 30. The system 10 may then determine a path along which a wavefront is heading by identifying the surrounding electrode 30 having an activation time closest to the activation time of the centrally-positioned electrode 30. The wavefront will likely be traveling along the determined path towards the electrode 30 that has the later activation time (of the surrounding electrode 30 and the centrally-positioned electrode 30). As for electrodes 30 on the outermost loop of the distal end 28 in the spiral configuration, data may need to be acquired from nearby locations before such a determination is made.

Figure 11:
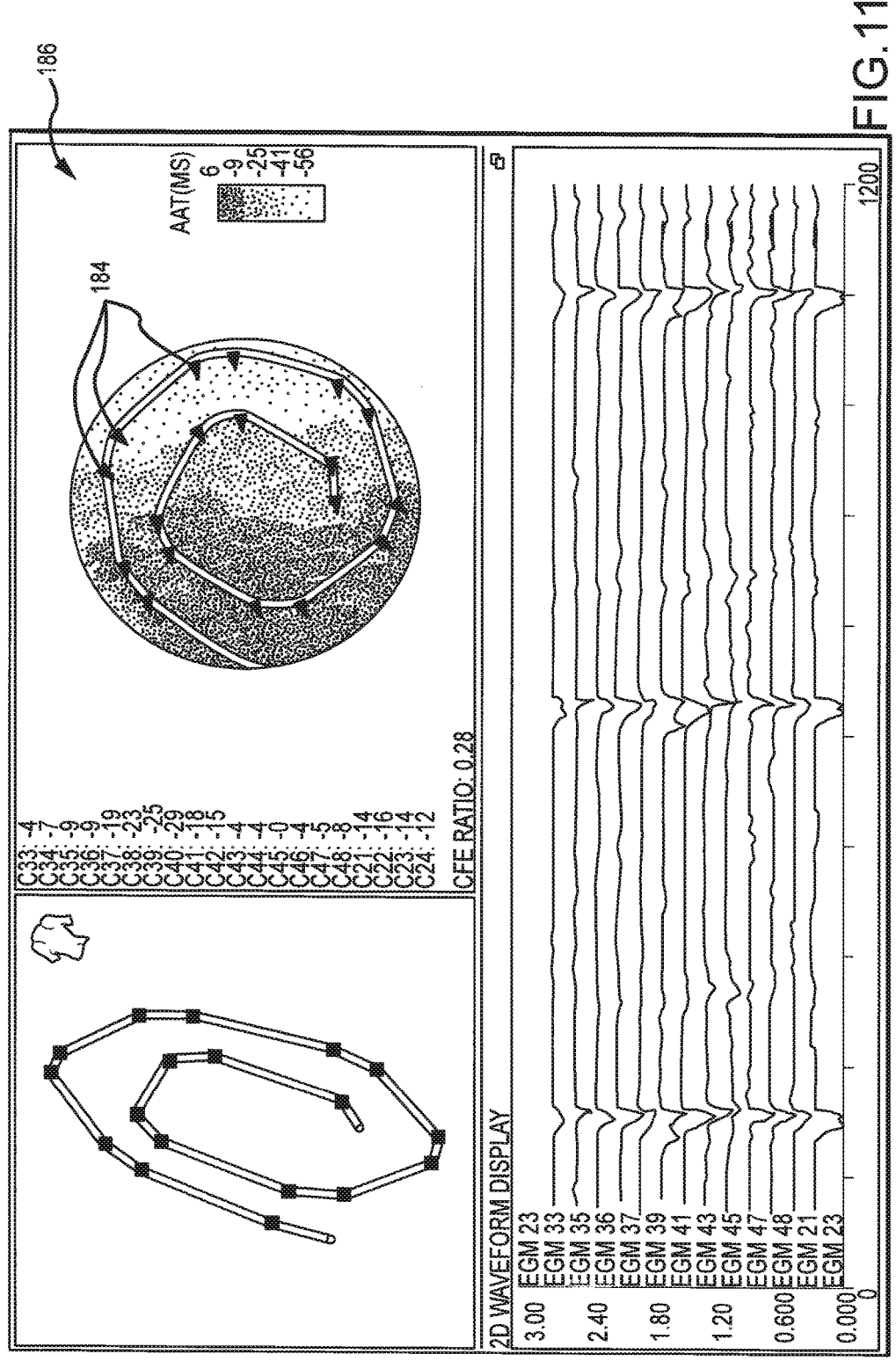
FIG. 11 is a portion of an exemplary graphical user interface (GUI) showing a configuration of sensors, EP data as acquired from tissue, and electrograms representative of the sensors.

In another example, the ECU 100 may compute the speed with which the depolarization wave travels from a first electrode ($e_1$) to a second electrode ($e_2$). The speed between $e_1$ and $e_2$ can be formulated by a vector in the 3D coordinate system. The direction, then, is defined as:

$$\vec{N} = \frac{\vec{V}}{|\vec{V}|}, \text{ where}$$

$$\vec{V} = (x_{e_2} - x_{e_1}, y_{e_2} - y_{e_1}, z_{e_2} - z_{e_1})/t_{e_2} - t_{e_1}$$

is the cardiac conduction speed measured between $e_1$ and $e_2$. In FIG. 11, the arrows 184 on the top right rendering window 186 represent the direction of cardiac activity at one snapshot. The arrows can be grouped in space (e.g., per quadrant and the whole catheter). These arrows 184 are consistent with the AAT color mapping discussed above.

In the alternative, the ECU 100 may compute the velocity with which the depolarization wave travels from the $e_1$ to $e_2$ using the following equation:

$$Velocity_{e_1 \to e_2} = |\vec{V}| = \frac{\sqrt{(x_{e_2} - x_{e_1})^2 + (y_{e_2} - y_{e_1})^2 + (z_{e_2} - z_{e_1})^2}}{t_{e_2} - t_{e_1}},$$

the ECU 100 may divide the distance between the first electrode ($e_1$) and the second electrode ($e_2$) by the difference between a first time ($t_{e_1}$) at which a depolarization wave passes the first electrode ($e_1$) and a second time ($t_{e_2}$) at which the depolarization wave passes the second electrode ($e_2$). By computing this metric for all adjacent electrodes 30 of a measured region, the ECU 100 can determine the velocities with which depolarization waves travel between multiple points on the tissue 12. In an alternative embodiment, conduction velocity values may also be computed from a temporal gradient of activation time.

Still other metrics may involve spatial and temporal gradients. Gradients are inherently noisy and demand densely sampled and clean data. Thus, the ability to compute gradients is largely possible because of the high density of electrodes 30 disposed on the distal end 28. Spatial gradients aim to identify locations where there is an abrupt change in scalar quantity over a spatial range, while temporal gradients aim to identify locations where there is an abrupt change in scalar quantity over a given time.

One example of a 2-D temporal gradient involves computing the derivative of a conduction velocity metric with respect to time. One resultant value of the measured region is shown generally by $$\frac{d(v_{1,2})}{d(t)},$$

where t represents a change in time and $v_{1,2}$ represents conduction velocity between a first electrode location and a second electrode location. This resultant value may represent the acceleration or deceleration of a depolarization wave traveling between two electrodes 30, one at the first electrode location and one at the second electrode location. As with most other metrics, the ECU 100 may be configured to compute this derivative metric for all the interpolated data of the HD grid 144, and then display the resultant values in the form of an HD surface map associated to the geometrical anatomical model 120 for display on the display device 102. An area showing a high rate of change may be an area of interest. For example, this area may represent a portion of the tissue 12 having scar tissue. Similar computations can be used to compute spatial gradients.

Two gradients of particular importance include spatial gradients of depolarization PP (peak-to-peak) amplitude and activation time. A spatial gradient of depolarization PP amplitude originates from a depolarization PP amplitude metric or an optimal bipolar electrogram. A depolarization PP amplitude metric may indicate the PP amplitude that an electrode, such as one of the electrodes 30, measures during each depolarization at a location in tissue 12. Spatially mapping the resultant values of this metric could show the spatial distribution of PP amplitudes in a region based on multiple electrodes 30. In one exemplary embodiment, the ECU 100 may consistently update an HD surface map on the display device 102 with each new PP amplitude that is less than a threshold value filter.

Further, mapping the spatial gradient of depolarization PP amplitude may also show the change in PP amplitude at each electrode 30 (or vertex of HD grid 144) with each sequential depolarization wave. Areas of the tissue 12 experiencing relatively consistent PP depolarization amplitudes will show minimal values, if any, when the spatial gradient of PP depolarization amplitude is mapped. By contrast, areas of the tissue 12 experiencing considerable change in PP depolarization amplitudes will show high values on the HD surface map. These heterogeneous areas may be areas of interest. Similar gradient metrics may be computed for activation times, and other characteristics of the tissue 12.

Another metric that the ECU 100 may be configured to calculate is a consistency metric. The consistency metric generally indicates whether resultant data from a primary metric is consistent or not. Many metrics exist from which to calculate the consistency metric. The consistency metric may be used to determine stationary characteristics of the electrogram depolarization and cardiac wavefronts. This metric may, in some embodiments, be calculated from the standard deviation (std) equation shown below:

$$std = \sqrt{\frac{\sum(S-\bar{S})^2}{N}},$$

where "S" represents the natural log value of each computed resultant value from the primary metric, "$\bar{S}$" is the mean of the natural log values of the calculated resultant values, and "N" is the number of calculated scale values. Another way to express this consistency metric is with the relative standard deviation, which is defined as std divided by the mean of the log values, can also be used for consistency analysis. The relative standard deviation may be more meaningful and precise to compare different measurements than std.

Moreover, the consistency metric may be computed by spatial grouping or by temporal grouping. For example, the set of computed resultant values from which "S," "$\bar{S}$," and "N" are obtained may be the PP depolarization amplitude metric values measured at an instant in time. Hence the computed standard deviation would represent the deviation in values across the spatial region from which the PP depolarization amplitude metric was computed. In another example, the set of scalar values from which "S," "$\bar{S}$," and "N" are obtained may involve a series of time sequential PP depolarization amplitude metric values from one particular electrode 30 on the distal end 28. Hence the computed standard deviation would represent the deviation in values produced by one electrode 30, and thus one location in tissue 12, over a period of time. In a further example, combinations of spatial groupings and temporal groupings may be combined.

Let $[s_1^t, \ldots, s_M^t]^T$ be a column vector representing the metric values of M sensors at time t. The ECU 100 may sample the system at different times, for example, $t_1, \ldots t_N$. Combining all N samples yields a M×N matrix:

$$s = \begin{bmatrix} s_1^{t_1} & \cdots & s_1^{t_N} \\ \vdots & & \vdots \\ s_M^{t_1} & \cdots & s_M^{t_N} \end{bmatrix}.$$

The ECU 100 may apply a principal component analysis to the matrix. The eigenvaules of the matrix may indicate how stable the measurements will be over time. Ideally, only the first eigenvalue will be nonzero because the rank of the matrix is one. The ECU 100 may compare the first eigenvalue with the summation of the other eigenvalues. The more dominant the first eigenvalue, the more consistent the measurement.

More generally, EP data that leads to resultant metric values having a low consistency may indicate an area of interest. Resultant metric values having a low consistency suggest that at least one aspect of the EP data may change with each successive depolarization wave. For example, a consistency metric may be computed based on a series of LAT metric values from a set of electrodes 30. If the resultant LAT values have a high consistency, or in other words, a low standard deviation, this means that the LAT values remain fairly constant from one depolarization to the next. If, however, the resultant LAT values have a low consistency, or in other words, a high standard deviation, this means that the LAT values are fluctuating from one depolarization to the next. Accordingly, a user may want to further probe areas of interest providing low consistency resultant data.

In one embodiment, the consistency metric may be computed as an HD surface map to be associated with the geometrical anatomical model 120, particularly where a consistency metric is computed for each electrode 30 location. In another embodiment, the consistency metric may be shown as an additional legend or statistic appearing near an HD surface map.

Another aspect of the system 10 concerns its ability to algorithmically combine two or more metrics computed from the same area of tissue 12 to form a composite map. All of the aforementioned metrics, even standing alone, may be very helpful in locating areas of interest. Under certain conditions, though, it may be even more valuable to combine two or more of these metrics to form a composite map. Composite maps, which originate in some embodiments from combining the resultant data from two or more metrics, may show where metrics reinforce one another where they are largely in agreement. For example, two gradients may mutually reinforce one another where their vectors largely agree on (a) the velocity and direction of activation, and (b) the rate of rise of amplitude near a breakout site. In some embodiments, the resultant values of combined metrics may be associated with the geometrical anatomical model 120. In other embodiments, the resultant values may serve as indicia of confidence, consistency, or validity of other computations.

A wide variety of metrics can be combined to provide further insight regarding the tissue 12. For example, combining several spatial gradients having high rates of amplitude change may be predictive of arrhythmia initiation and termination sites since these combinations highlight regions of rapidly growing amplitude (arrhythmia breakout or focal origination) or rapidly shrinking amplitude (arrhythmia disappearance, break-in, or block). As a further example, combining a spatial distribution of activation amplitude and a temporal pattern of depolarization may facilitate the identification of reentrant or ectopic arrhythmia sites. Still another example involves combining at least two high spatial gradients of amplitude to show arrhythmia initiation and termination. Yet other examples include combining electrogram amplitude with a temporal gradient of depolarization, combining early activation time and lowest voltage, and combining LAT and PP metrics.

One possible way to combine scalar metrics into a composite map is to normalize the data, weight the data, and combine the data to form a composite map. This can be done even if the resultant data values from the primary metrics are in different units. A user or the ECU 100 may select ranges (e.g., low to high) for the resultant data values from at least two metrics. Based on these ranges, the resultant data values from the metrics may be normalized to correspond to values between zero (0.0) and one (1.0). Likewise, the user of the ECU 100 may assign a weight to each metric to achieve an appropriate blend of influence. Next, the normalized values may be combined by the following equation:

$$C = W_1 \times M_1 + W_2 \times M_2,$$

where C represents the new composite value, $W_{1,2}$ represent weights assigned to each metric, and $M_{1,2}$ represent scalars of the primary metrics.

A similar combination can be made with vector metrics by taking, in a most basic form, the dot product of two primary metrics. Low or negative values in the dot product may indicate substantial disagreement and the untrustworthiness of sites involved with arrhythmia breakout, disappearance, or ectopy.

Similar to the practice of weighting some metrics more than others in metric combinations, the ECU 100 may weight some EP data more so than other EP data. Mapped data values may be weighted, for example, by proximity to various anatomical or functional anatomical structures. This may be the case whether the mapped data values are computed from an individual metric, a derivative metric, or a combination of metrics. As a further example, in the case of contact mapping catheters, the ECU 100 may receive data regarding which electrodes 30 are sufficiently proximate to the tissue 12. The ECU 100 may weight the electrodes 30 that are in sufficient proximity to the tissue 12 more heavily than those electrodes 30 that are not sufficiently proximate to the tissue 12. The weights, however, should add up to one. By weighting metrics, the ECU 100 ensures that only sufficiently reliable data is used in mapping, representing, and analyzing the tissue 12.

As a further aspect of the system 10, EP data may also be used to identify a depolarization wavefront pattern on the tissue 12. The ECU 100 may even be configured to recognize multiple wavefront patterns that may exist during cardiac activation, especially with complex arrhythmias. Identifying wavefront patterns can be important because it can lead a user to areas of interest along the tissue 12. Depolarization wavefronts may, in some cases, reach some locations in the tissue 12 that are further away from the source of the wavefront sooner than locations that are closer to the source (e.g., because of a short circuiting effect). In some of these cases where a point on the tissue 12 experiences two wavefronts, it may seem as if there is more than one source of depolarization.

In other cases, two or more sources of depolarization wavefonts may actually exist. Normal depolarization waves originate from cells in either the sinoatrial node, the atrioventricular node, the Bundle of His, or Purkinje fibers. Though not typical, cardiac muscles are also capable of producing electrical impulses that turn into depolarization waves. Thus more than one depolarization wave may traverse the tissue 12. Identifying sites of arrhythmia breakout allows the user to target this location for treatment.

Figure 12:
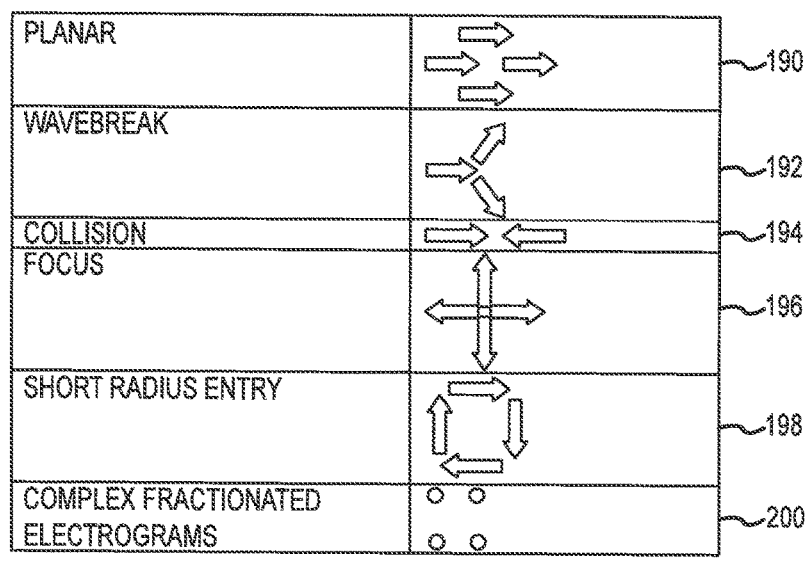
FIG. 12 is a table showing several categories of exemplary wavefront patterns that a system uses to identify depolarization wavefronts on measured tissues.

As shown in FIG. 12, several exemplary wavefront patterns may include, for example and without limitation, planar 190, wavebreak 192, collision 194, focus 196, short radius entry/reentry 198, and CFEs 200. Additional patterns (not shown) may include, for example and without limitation, pivot and rotor wavefronts. To classify the wavefront pattern, the ECU 100 may algorithmically combine the known spatial electrode 30 configuration of the distal end 28, the position coordinates of the distal end 28, the electrograms, and timing data.

Wavefront pattern recognition may be implemented using matched filters. Although the algorithm is described in the 2D coordinate system, it can be extended to a 3D coordinate system using linear transformation. Let $\{(x_1, y_1), \ldots, (x_n, y_n)\}$ be the coordinates of some n sensors defined in the manufacturing specification. Let $\{(\hat{x}_1, \hat{y}_1), \ldots, (\hat{x}_n, \hat{y}_n)\}$ be the coordinates of n sensors measured in the ECU 100. Let $P^1 = \{\theta_1^1, \ldots, \theta_n^1\}, \ldots, P^m = \{\theta_1^m, \ldots, \theta_n^m\}$ be m patterns, and $\theta_i^j$ stands for cardiac direction of the $i^{th}$ sensor on the $j^{th}$ pattern. Let $\hat{P} = \{\theta_1, \ldots, \theta_2\}$ be the cardiac activation direction of sensors measured in the ECU 100. The matching process can be implemented as follows:

Find the center of $\{(x_1, y_1), \ldots, (x_n, y_n)\}$ and $\{(\hat{x}_1, \hat{y}_1), \ldots, (\hat{x}_n, \hat{y}_n)\}$ by averaging, making sure both coordinates have the same center.

Rescale $\{(x_1, y_1), \ldots, (x_n, y_n)\}$ and $\{(\hat{x}_1, \hat{y}_1), \ldots, (\hat{x}_n, \hat{y}_n)\}$ so that they will have the same scales. After shifting and scaling, the only degree of freedom is the rotation angle $\alpha$. Let $\{(\hat{x}_1^t, \hat{y}_1^t), \ldots, (\hat{x}_n^t, \hat{y}_n^t)\}$ be the coordinates after modifying the shift and scales of $\{(\hat{x}_1, \hat{y}_1), \ldots, (\hat{x}_n, \hat{y}_n)\}$.

Start at $\alpha_0$ and increase by $\delta_\alpha$ at the $t^{th}$ step.

Rotate coordinates in $\{(\hat{x}_1^t, \hat{y}_1^t), \ldots, (\hat{x}_n^t, \hat{y}_n^t)\}$ by $\alpha_0 + t \delta_\alpha$.

Find $(\hat{x}_i^t, \hat{y}_i^t)$, corresponding coordinates on the model $(x_j, y_j)$.

Compute the summation of difference $\text{diff}(t,k) = \Sigma |\theta_i - \theta_j^k|$ between the measured pattern and the $k^{th}$ predefined pattern.

Select the pattern that has the minimum $\text{diff}(t,k)$, $\forall t, k$.

This method is just one example of how to determine the optimum pattern in real-time. And further, $\delta_\alpha$ can be adjusted to tradeoff the performance for computational cost.

As this input is acquired and compiled (e.g., into matrices or databases), the ECU 100 may continuously document the comparative timing differences between each neighboring electrode 30 and apply a number of filters to this compiled data. The filters may be looking for patterns in these compilations of data corresponding to wavefront patterns, some of which are shown in FIG. 12. These filters may be matched spatial filters in some embodiments, and may be configured to recognize patterns in the compilations in a variety of directions, orientations, sizes, etc. By using filters on this set of input data, the ECU 100 can identify and classify various depolarization wavefront patterns traveling across the tissue 12.

Using the various computed metrics and wavefront pattern classifications, the ECU 100 may identify and highlight on the display device 102 an anatomical site that is suspected of maintaining atrial fibrillation, as described below. Moreover, the ECU 100 may compute and display such visual aids in both 2-D and in 3-D. Visual aids in 3-D may be particularly helpful for areas of the tissue 12 that are damaged.

Figure 13:
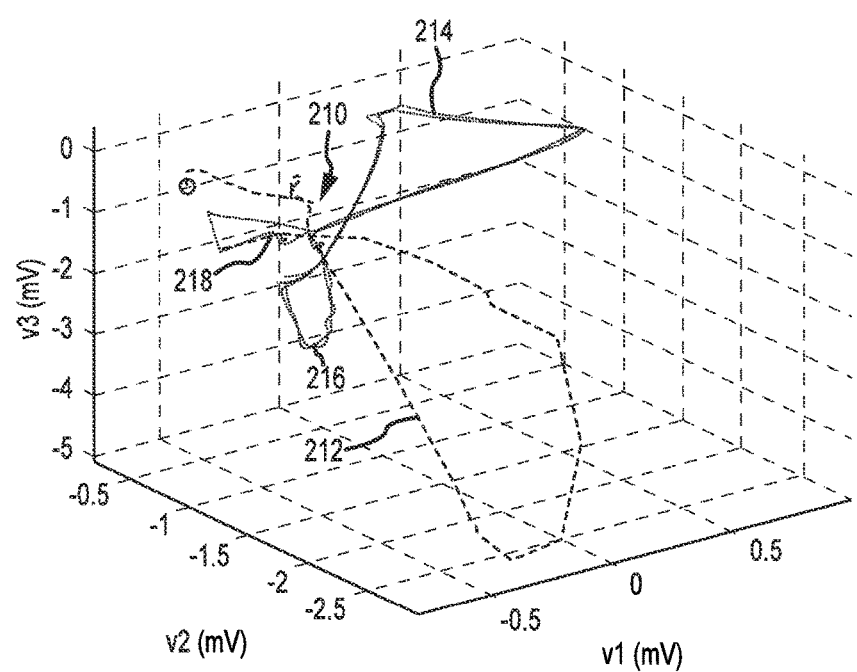
FIG. 13 is an exemplary three-dimensional graph representing voltages in milli-volts (mV) measured with respect to three different directions.

In an exemplary embodiment, the spot electrodes $30_B$ and the distal ring electrode $30_C$ of the ablation tip 80 shown in FIG. 5 may be said to be in a tetrahedron-like arrangement, where the distal ring electrode $30_C$ is represented by a geometric centroid. This tetrahedron-like arrangement allows local bipolar electrogram signals to be spatially resolved into 3-D space with respect to the ablation tip 80. From this set of electrode data, which may not necessarily be orthogonal, a linear transformation may put the bipolar vector electrograms into a 3-D orthogonal coordinate frame, as shown in FIG. 13, based on the ablation tip 80. In an alternative embodiment, the 3-D vector electrogram may be associated to the geometrical anatomical model 120 since the electrode orientation and position of the ablation tip 80 are also known. Other configurations can also be used to obtain similar results.

Referring to the 3-D graph in FIG. 13, the electrical potential magnitude (measured in milli-volts (mV)) of the tetrahedron-like electrode arrangement from the ablation tip 80 is shown with respect to three different directions (v1, v2, and v3). The 3-D vector electrogram spends time near an origin 210 during isoelectric periods and shoots out in various directions with depolarization and repolarization. One loop 212 is the result of an ectopic beat, and its depolarization direction is predominantly in the negative v2 direction. Another loop 214 shows a stable baseline cardiac rhythm having a depolarization direction instead in a predominantly positive v1 direction. To acquire data from normal and ectopic beats, the ablation tip 80 may be left at a location in or on the tissue 12 until both states of arrhythmia and non-arrhythmia occur.

In addition to the dominant loops, other deflections may exist. Some deflections, such as the deflection 216, may result from a far-field depolarization or near-field repolarization. Low amplitude fractionated activity appear as small, irregular deflections around the isoelectric point, such as the deflection 218. Still other data, such as that originating from locations near the center of a rotor wavefront, may appear on this type of graph as a rotating trajectory, "orbiting" around an isoelectric point.

Still other aspects of the system 10 relate to the display device 102 and to preventing data of a marginal quality from being used by a user or the ECU 100.

Figure 14A:
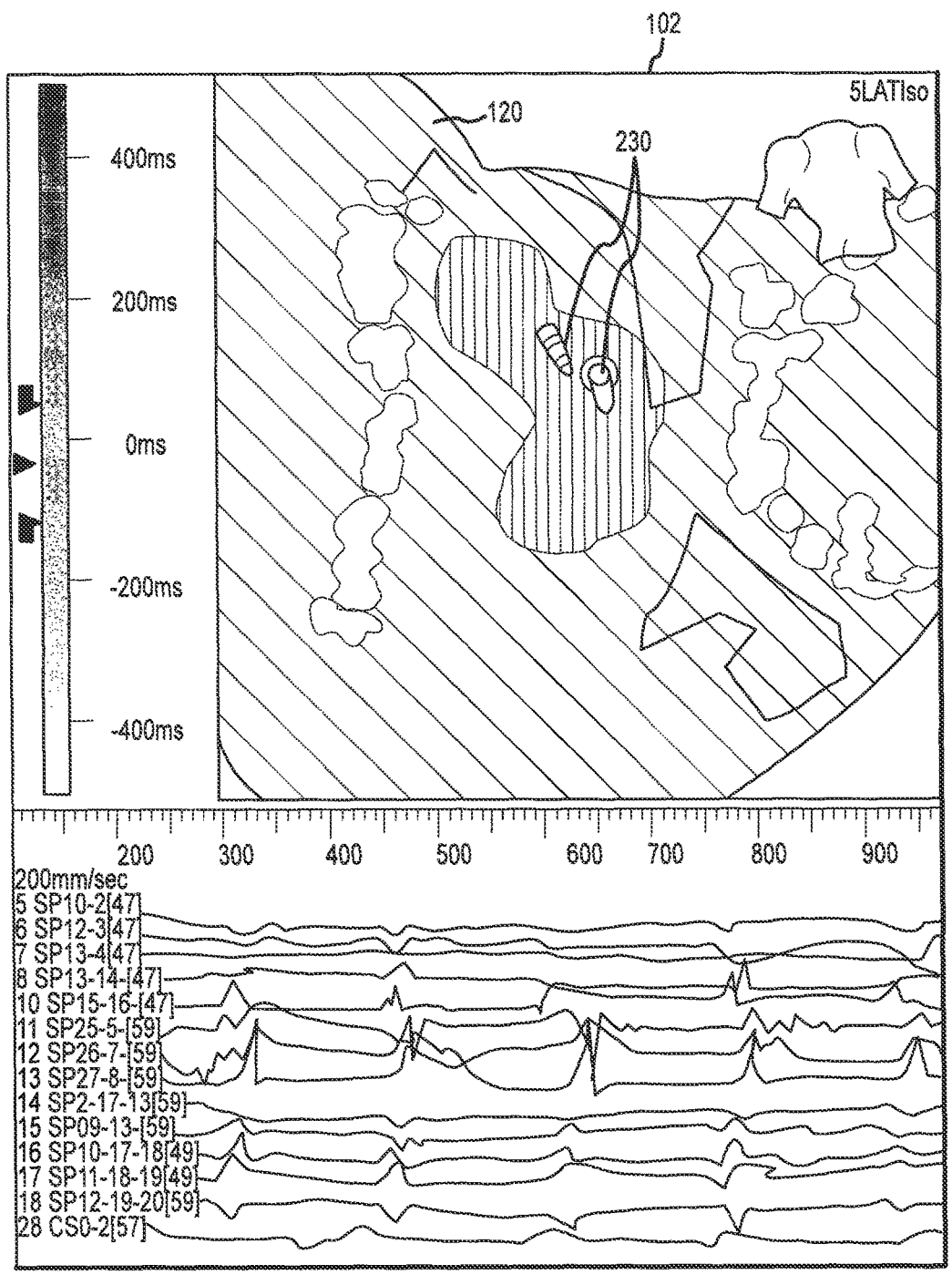
FIGS. 14a-14d are exemplary representations of electrograms and maps showing increments of data that are displayed by an electronic control unit (ECU) as a distal end of a medical device measuring electrophysiological data approaches tissue from a body.
Figure 14B:
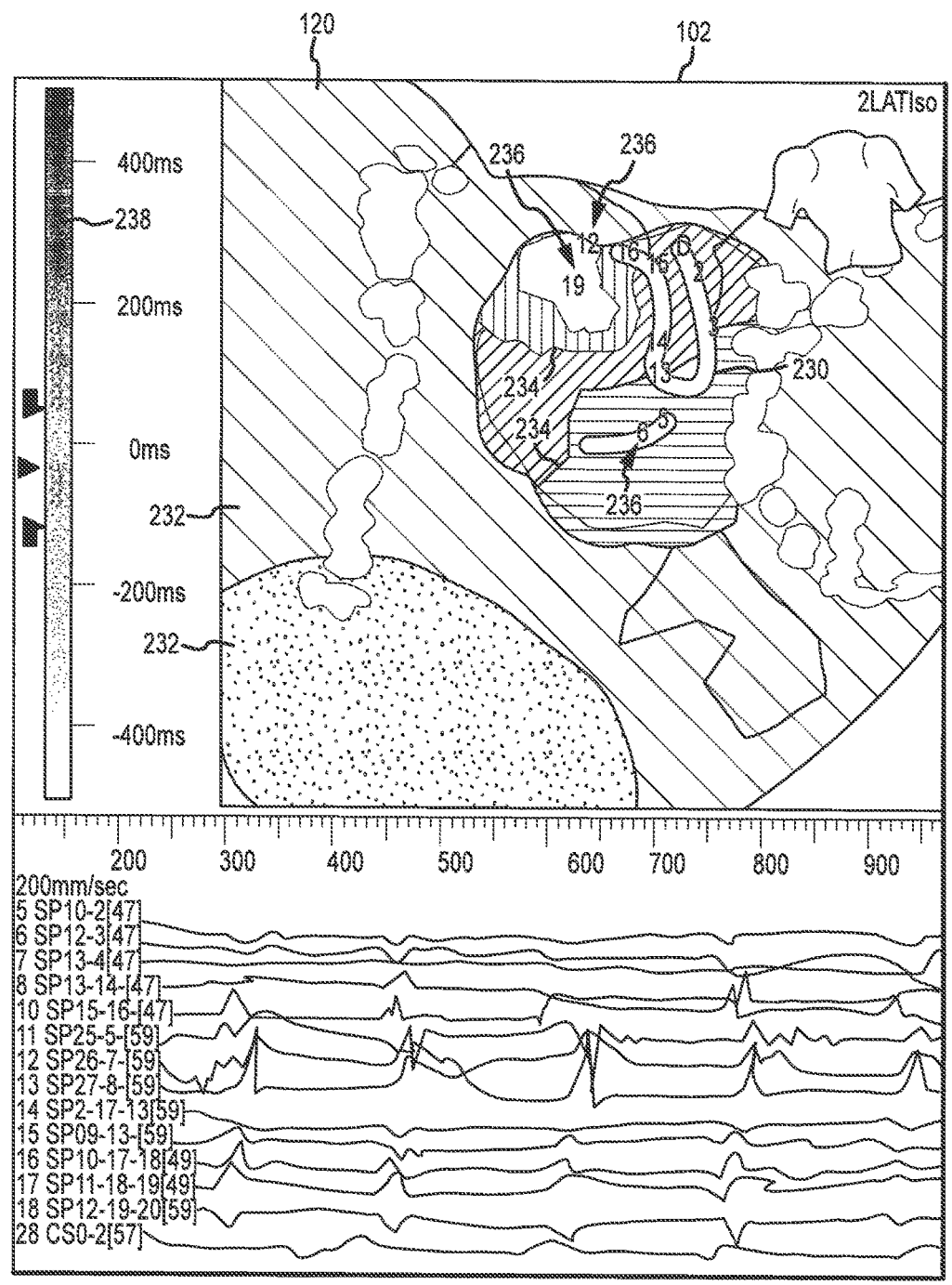

The ECU 100 may include another exemplary quality control feature in addition to, or in place of, the quality control measure, as described with reference to FIGS. 10a-10b, of limiting the display of representation 180 until the distal end 28 is sufficiently close to the tissue 12 such that the metrics are computed based on quality EP data. Accordingly, as shown in FIG. 14a, the ECU 100 may display, in relation to the geometrical anatomical model 120, only those portions of the distal end 28 that are positioned sufficiently close to the tissue 12. In addition, when the distal end 28 is not sufficiently close to the tissue 12 to measure quality EP data, portions 230 of the distal end 28 may be totally transparent or translucent. As the distal end 28 approaches the tissue 12, portions 230 may become less transparent, as shown in FIG. 14b. Displaying only sufficiently close portions 230 and/or using transparency can signal to the user whether the distal end 28 is sufficiently close to the tissue 12.

The embodiment shown in FIG. 14b depicts out-of-range colors 232 that may be chosen to indicate values that are out of a range of interest. It may be helpful to additionally, or in the alternative, associate contour lines of constant index value with the geometrical anatomic model 120. Contour lines can highlight the boundaries between areas displaying different values. In the case of activation time mapping, for example, these contour lines are referred to as isochrones 234. Likewise, it may be helpful to superimpose numeric values 236 to the geometrical anatomical model 120 to help identify displayed data values within certain colored and/or non-colored regions without reference to a legend 238. In addition, or in the alternative, the legend 238 may indicate the range of values that correspond to the various displayed colors. The ECU 100 may also show on the display device 102 the inclusion of markers, labels, or annotations, some of which may be user-authored, to help track prior ablation sites or anatomic or functional locations of relevance to electrophysiology procedures, for example. Further examples may include marking sites of blockage, slow conduction, low voltage, and fractionation.

Figure 14C:
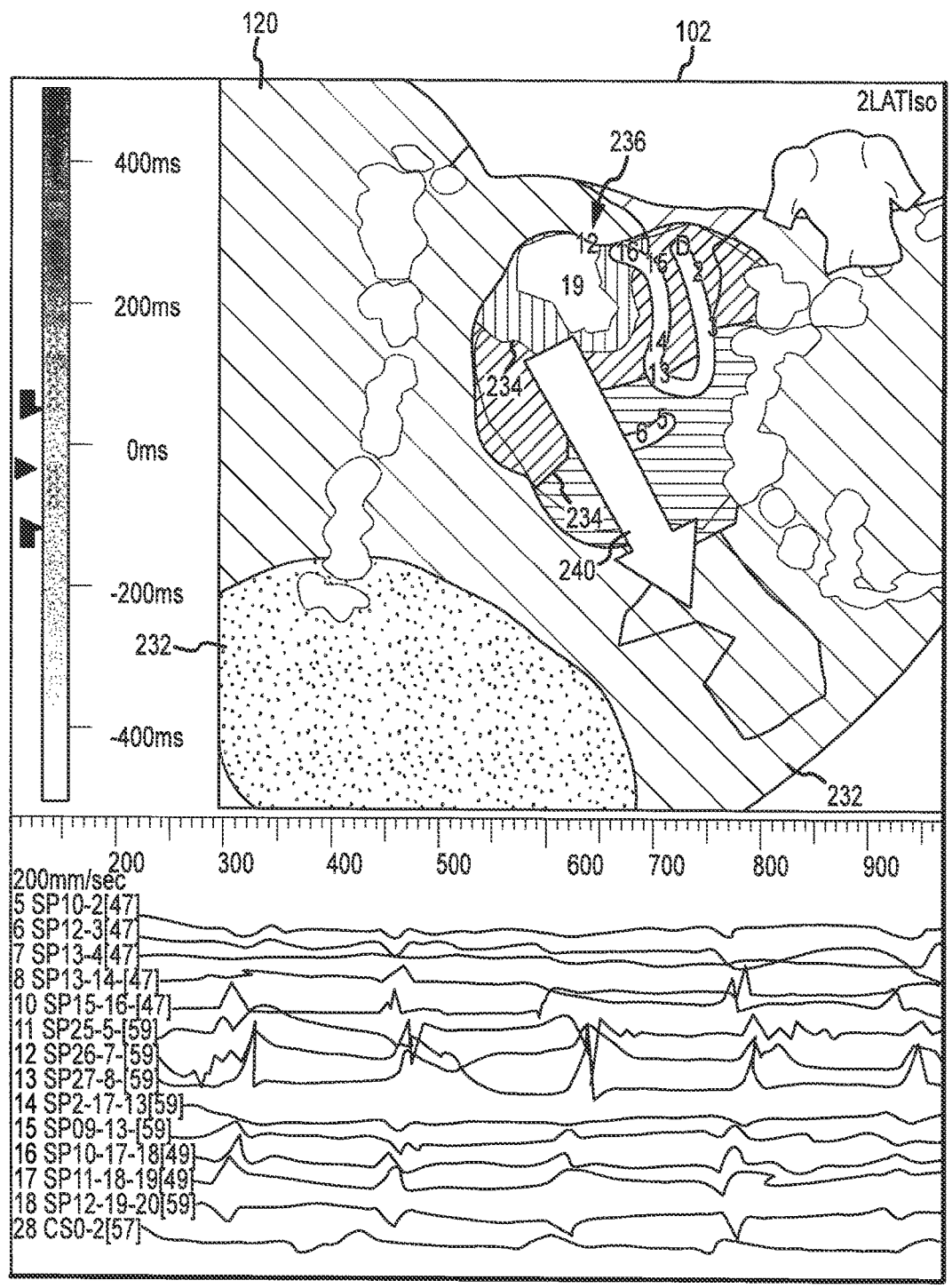
Figure 14D:
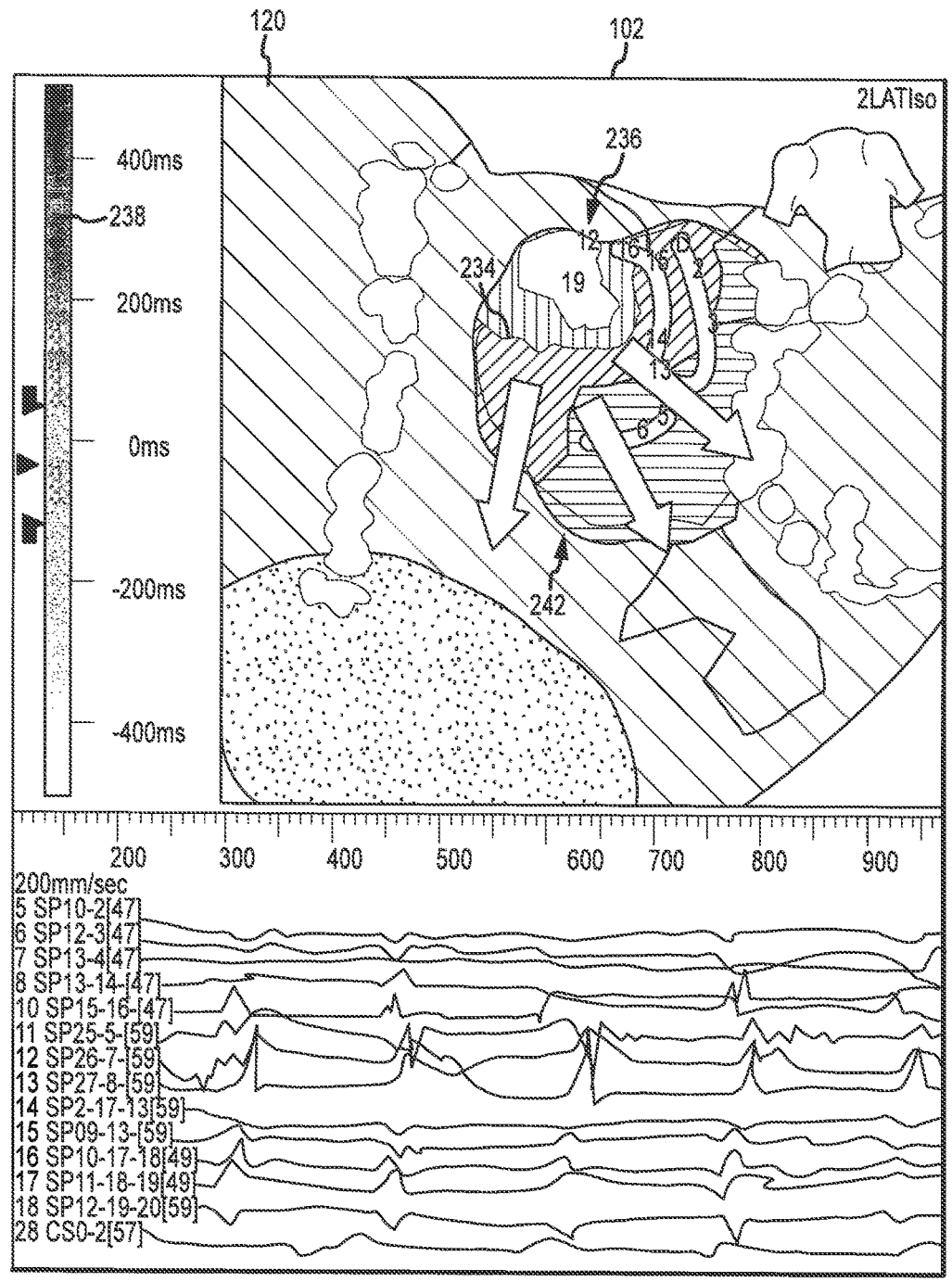

As the distal end 28 approaches the tissue 12, the ECU 100 can use more reliable EP data to perform more computations and provide the user with more information. FIG. 14c shows a representation in the form of a vector 240 indicating the general direction and velocity magnitude of depolarization conduction traversing the tissue 12. The vector 240 may represent the wavefront for one electrode 30, for a subset of electrodes 30, for all electrodes 30 on the distal end 28, or for electrodes 30 from distal ends of numerous catheters. Wavefronts having large conduction velocities may be shown with larger vectors 240, though wavefronts having small conduction velocities may be shown with smaller vectors 240. As the distal end 28 approaches the tissue 12, the ECU 100 may generate the vector 240 by computing metrics based on the comparative timing and voltage differences between each neighboring electrode 30. FIG. 14d shows how the ECU 100 may provide even more detail related to a possible wavefront pattern 242 as additional EP data is measured from a position of the distal end 28 that is closer to the tissue 12.

As described above, the ECU 100 may be configured to prevent data of a marginal quality from reaching display device 102. In such an embodiment, the ECU 100 prevents decisions from being made based on data of a marginal quality. Instead, the ECU 100 encourages users to obtain additional good data when needed. Similarly, in metric calculation, the ECU 100 may be configured to not use data below a certain confidence threshold. For example, upon the receipt of proximity data, the ECU 100 may discard data acquired from a distance that is too remote from the tissue 12. Under this mode, the display device 102 would only display data from a qualified subset of all EP data.

As also discussed above, in some embodiments, the anatomical model 120 and HD surface maps, such as the vector 240 or the wavefront 242, may be updated with each subsequent reference signal trigger. In other embodiments, the anatomical model 120 and HD surface maps may be refreshed instantly, or as fast as the system 10 will allow.

While the physical screen of the display device 102 may be refreshed frequently, visual aids (e.g., HD surface maps, markers, labels, annotations, and the like) may persist on the display device 102 for periods of time. A user may control through the user input device whether and how long visual aids may persist. In some embodiments, visual aids may remain visible even after the distal end 28 has moved away from an area of the tissue 12. In other embodiments, however, the visual aid may only persist on the display device 102 while the distal end 28 remains within a certain area of the tissue 12. In yet another embodiment, the user may configure the system 10 such that visual aids remain visible on the anatomical model 120 for a fixed amount of time after the distal end 28 has moved away from the tissue 12. Still another embodiment may involve maintaining only certain visual aids once the distal end 28 has moved away from a location of the tissue 12. For example, it may be helpful to maintain only user-authored annotations on the display device 102 as regions of data are spatially cataloged. As a further example, only computed conduction vectors and wavefront pattern classifications, such as those in FIGS. 10b and 12, may be maintained on the display device 102.

The system 10 is unlike conventional sequential activation mapping systems, particularly in embodiments where electrograms, metrics, HD surface maps, and generally EP data from the tissue 12 are cataloged onto the same geometrical anatomical model 120. For example, one difference is that as regional acquisitions are taken with the distal end 28, the nature of the multiple HD surface maps being compiled can be asynchronous. In other words, unlike conventional synchronous procedures, the system 10 does not require a fixed reference to which activation times of regional acquisitions measured during different cardiac phases are absolutely indexed. Accordingly, all activation data need not be fiducially aligned. Instead, each regional acquisition may include information regarding relative timing differences within that region.

The multiple HD surface maps from different regions may be catalogued asynchronously because oftentimes in complex arrhythmias, numerous depolarizations occur, as described above. During atrial fibrillation, for example, pathologic electrograms very often contain split potentials, mid diastolic potentials, and low voltage fractionated depolarizing activity. The ECU 100 may prevent any overlap between regions as regional EP data acquisitions are spatially cataloged since activation patterns from one region to another may be asynchronous. It follows that maintaining the display of regional boundaries or even lines of block (i.e., separating two adjacent sampled regions by at least fifty milliseconds of delay) may also be desirable.

With respect to various HD surface maps, such as, AAT mapping and wavefront pattern mapping, for example and without limitation, a beat buffer may be provided where the user can view how a map changes from one beat to the next and so on. To illustrate with wavefront mapping, the user may select a timeframe in which to sample EP data. In one exemplary embodiment, the timeframe may be, for example, ten seconds. The ECU 100 may then input this data into a number of algorithms, resulting in computed wavefront patterns that may be displayed as HD surface maps, such as the map of 2-D vectors 182 in FIG. 10b, for example. After computing such patterns for the number of beats that occur during this ten second timeframe, the user could view this ten second sequence of beats on the display device 102. The user could note the changes, cycles, trends, etc. that occur from one beat to the next during this timeframe. The ECU 100 may provide an option for the user to accelerate or decelerate this viewable sequence. The ECU 100 may also provide an option where the user would need to interact with the display device 102 each time the user desires to advance the view to the next sequential heartbeat. For example, before advancing to each successive sequence, the GUI 122 could prompt the user to advance the sequence via the user input device. Moreover, because of the high density of electrodes 30 disposed on the distal end 28, the entire HD surface map may update with each beat. Still further, this feature may be particularly helpful when ablation therapy is being performed because characteristics affecting depolarization paths may be affected by the treatment.

Another aspect of the system 10 involves providing the user with information on the display device 102 that may help direct placement of ablation lesions or more definitive diagnostic maneuvers including, for example, therapy delivery and pace mapping. Therapy delivery may involve a procedure such as, for example, an ablation procedure, and pace mapping may involve reproducing a cardiac activation sequence generated by a particular arrhythmia. In manual interventions such as these, the acquired EP data may originate from the therapy delivery instrument or the pacing instrument. The system 10 may utilize the various computed metrics, composite maps, other visual aids, and quality control features (e.g., transparency) based on the therapy delivery instrument or the pacing instrument to help guide a user through a procedure.

The user may select an ablation or definitive diagnostic targeting criterion appropriate for the arrhythmia, chamber, and clinical situation, which may include appropriate threshold values, map type, and composite indices, for example. A field of many arrows describing patterns of conduction and electrogram amplitude, or activation data, may be condensed, if needed, to a more specific graphical display of breakout or other target sites on the geometrical anatomical model 120. To use a condition of breakout as an example, one composite arrow may be derived from the mean direction and amplitude associated with the time of breakout. Uncertainty of data may be considered by introducing a weighted average that depends on the density of data, its signal quality, and agreement between amplitude and activation time gradients. The tail of this composite arrow may incorporate a target designation and may be superimposed over the geometrical anatomical model 120 where one or both gradients have large magnitudes. This may be achieved, for example, by computing a gradient magnitude centroid or finding a point of maximal gradient magnitude. The direction of the arrow may denote the predominant depolarization wavefront direction and/or direction of electrogram amplitude growth.

In an alternative embodiment, the target site may be designated by other visual cues such as coloring or texturing of nearby cardiac surfaces. This composite target arrow may be updated as often as on a beat-to-beat basis. This may be helpful especially when ablation is performed mid-procedure because after ablation, new EP data may be measured, processed, and incorporated into the existing composite target arrow and/or other HD surface maps. On the other hand, the composite target arrow may be updated at the discretion of the user. Further, the user may cause the target arrow to become stationary to facilitate comparisons and other evaluations.

Figure 15:
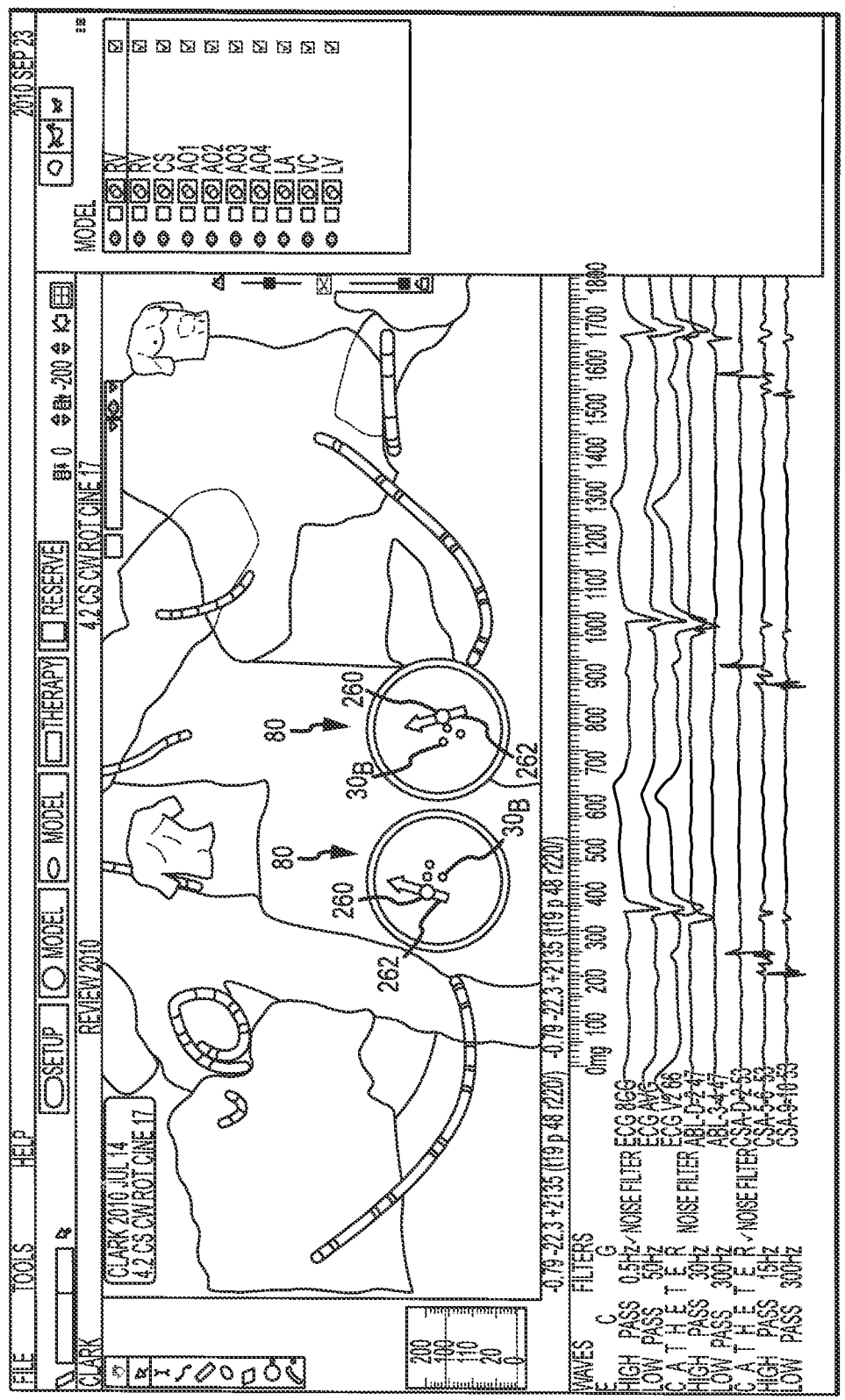
FIG. 15 is another exemplary representation of a display device of the system illustrated in FIG. 1 with a graphical user interface (GUI) displayed thereon.

In an exemplary embodiment, the ablation tip 80 of the distal end 28 may find particular use for the guidance features of the display device 102. FIG. 15 shows the positions of two ablation tips 80, particularly the ablation tip electrodes, which are superimposed onto the geometrical anatomical model 120 as projections 260. In an alternative embodiment, the projections 260 could represent a centroid of the tetrahedron-like arrangement of spot electrodes $30_B$ and the distal ring electrode $30_C$. Moreover, the centroid of the tetrahedron-like arrangement could also serve as a point that is represented by the 3-D map shown in FIG. 13. In any event, display of target arrows 262 may signify, for example, the mean direction and amplitude of a recent activation. The arrows 262 may not necessarily carry an explicit target, but the size of the arrows 262 may confer proximity to a target since the set of bipolar signals themselves depend on amplitude gradients and, via filtering, the speed of conduction.

Another advantage to the guidance features of the system 10 is that automated initial lesion placement or diagnostic mapping, for example, may also be facilitated. The distal ends 28 having the ablation tips 80 may be moved about, and through observation or map generation, an ideal position and values for ablation or pacing may be highlighted. For example, the ECU 100 may identify areas of scar tissue based on the results of computed metrics. Depending on the sizes and locations of scar tissue identified, the ECU 100 may highlight locations and propose intensities for corrective and/or preventative procedures. This feature could assist in mapping, planning, initial ablation therapy delivery, or more definitive diagnostic testing. Moreover, all the while, the HD surface maps, the arrows 262, and the visual aids in general may be updated based on the EP data measured by the distal end 28.

In addition to the advantages noted above, the system 10 may be useful in understanding macro reentrant rhythms in the Left Atrium (LA). Many patients are prone to developing this rhythm after electrophysiology procedures involving Pulmonary Vein Isolation (PVI). As mentioned above, the system 10 and the distal end 28 may help highlight the anatomical site within the tissue 12 maintaining the atrial fibrillation. Further, the system 10 may potentially provide localized substrate analysis of clinical value.

After performing various analyses of the tissue 12, the system 10 may also provide the user with options to save various types of work product for future use. For example, the system 10 may allow the user to save series of EP data, to assign names to dynamic maps, to store maps, and to retrieve maps so as to track distinct arrhythmias and the evolution of procedural progress. The system 10 could present the user with such options through the GUI 122 during or following the procedure(s). The user could then utilize the user input device to save data, maps, and the like to the ECU 100, to some removable computer-readable storage medium, to a server, or to any other storage device for subsequent retrieval.

It will be appreciated that in addition to the structure of the system 10, another exemplary aspect of the present disclosure is a method for measuring, classifying, analyzing, and mapping spatial patterns in EP data and for guiding arrhythmia therapy. It will be further appreciated that the methodology and constituent steps thereof performed and carried out by the ECU 100, and described in great detail above, apply to this aspect of the disclosure with equal force. Therefore, the description of the methodology performed or carried out by the ECU 100 set forth above will not be repeated in its entirety, rather several exemplary steps will be reiterated.

Generally, the ECU 100 may acquire a variety of fundamental input data coming primarily from both the visualization, navigation, and mapping subsystem 18 and the electrodes 30 of the distal end 28. Various types of input data may include, for example without limitation, the particular configuration of the distal end 28, the known electrode spacing of the distal end 28, coordinate positions of the electrodes 30, EP data from the electrodes 30, timing data corresponding to the EP data, and the geometrical anatomical model 120.

The ECU 100 may then interpolate the input data to the HD grid 144 and compute a number of scalar metrics. After interpolating and computing resultant metric values, these values may be associated with the geometrical anatomical model 120 and mapped in HD as a field of scalars. These HD scalar surface maps may include, for example, electrogram voltages, PP voltage amplitudes, LAT, CFE activity, and characterizations of the tissue 12 as assessed by the ECU 100 or a user.

The ECU 100 may also apply 2-D spatial derivative filters, 3-D temporal derivative filters, or 3-D spatial derivative filters to the input data and/or resultant scalar metric values to further obtain derivative data values. For example, after applying the filters, this derivative data may include 2-D and 3-D electrogram voltage vectors, 2-D and 3-D conduction velocities, 2-D amplitude gradients, CFE gradients, and 2-D characterizations of the tissue 12 as assessed by the ECU 100 or the user.

Figure 16:
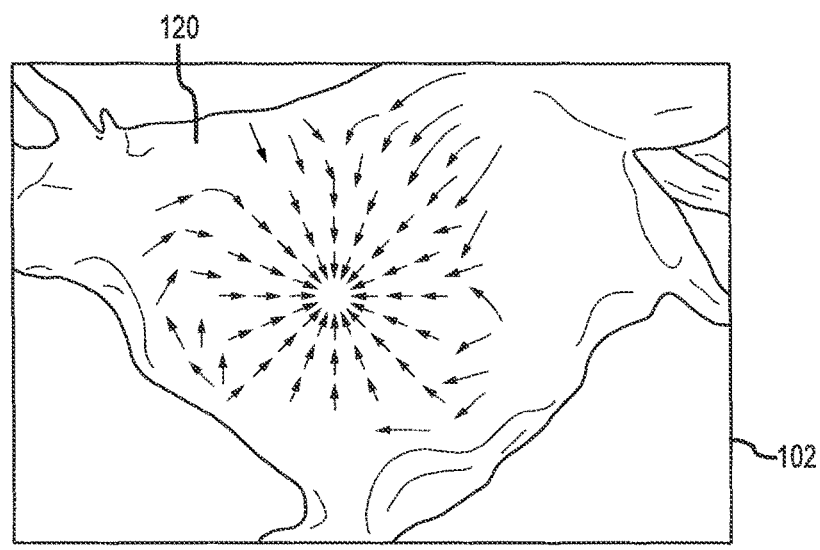
FIG. 16 is an exemplary representation of a surface map displaying a field of vectors with directional and magnitude significance displayed thereon.

From the derivative data, the ECU 100 may generate HD vector surface maps as shown, for example, in FIG. 16. HD vector surface maps may include gradient maps of conduction velocity, activation amplitude, CFE activity, and characterizations of the tissue 12, for example. In one embodiment, a gradient map may involve a vector field having numerous scalars pointing in directions of the greatest rate of change in the scalar field of data. The magnitude of such arrows may correspond to the rate of change.

As described above, the ECU 100 can use both scalar and vector resultant metric data values to generate HD surface maps. In another embodiment, the ECU 100 may use these data values to further compute composite metrics for display as HD composite maps. Scalar values from different metrics, which may otherwise be individually mapped as HD scalar surface maps, may be combined by normalizing values, weighting each metric as desired, and combining the values. One way to combine vector values from different metrics, which may otherwise be individually mapped as HD vector surface maps, is to compute the dot product of the two individual metrics.

Another aspect of the ECU 100 involves identifying depolarization wavefront patterns based on the resultant data values used to generate either HD scalar surface maps or composite maps. The ECU 100 may, in one embodiment, use a set of matched spatial filters to search in a multitude of directions, orientations, and sizes for patterns in the resultant data values stored in matrices, databases, or the like.

While much of the data displayed through HD surface maps is critical, it may be desirable to filter out other portions of noncritical data. Therefore, at the discretion of the user, the ECU 100 may be configured to apply a 2-D spatial gradient filter to the resultant data values used to generate either HD scalar surface maps or composite maps. A 2-D spatial gradient filter may be a matched spatial filter with a short spatial scale to detect critical spatial characteristics such as gradient. For example, a 2-D spatial gradient filter may be applied to data values or a scalar map itself to highlight only areas on the spatial map that are showing a great deal of change (e.g., electrogram voltage or LAT) over a short distance. In one embodiment, the user may specify the rates of change that should be returned from application of the filter.

Similarly, the ECU 100 may also apply a 2-D spatial "bridge" filter to the resultant data values used to generate either HD scalar surface maps or composite maps. A 2-D spatial bridge filter may be a matched spatial filter with large spatial scale. A 2-D spatial bridge filter may aim to detect spatial characteristics such as a bridge or isthmus in the data values. A rudimentary example of the type of pattern that a 2-D spatial bridge filter may locate is shown by the following:

$$\begin{vmatrix} 0 & 1 & 0 \\ 0 & 1 & 0 \\ 0 & 1 & 0 \end{vmatrix}$$

Therefore, 2-D spatial bridge filters may be helpful in detecting certain types of patterns in the EP data. These types of data may include, for example, low voltage areas surrounded by high voltage areas and low voltages surrounded by fixed anatomic block (slow conduction velocity). 2-D spatial bridge filter may be even more helpful when used in combination with other filters.

It should be noted that the ECU 100 may obtain the described metrics, maps, and composite maps in more than one way. For example, as opposed to computing the conduction velocity metric as described further above, the ECU 100 may apply a 2-D spatial derivative filter to an LAT map to obtain a conduction velocity map. As a further example, applying a 2-D spatial derivative filter to the conduction velocity map may result in a gradient of the conduction velocity.

Figure 17:
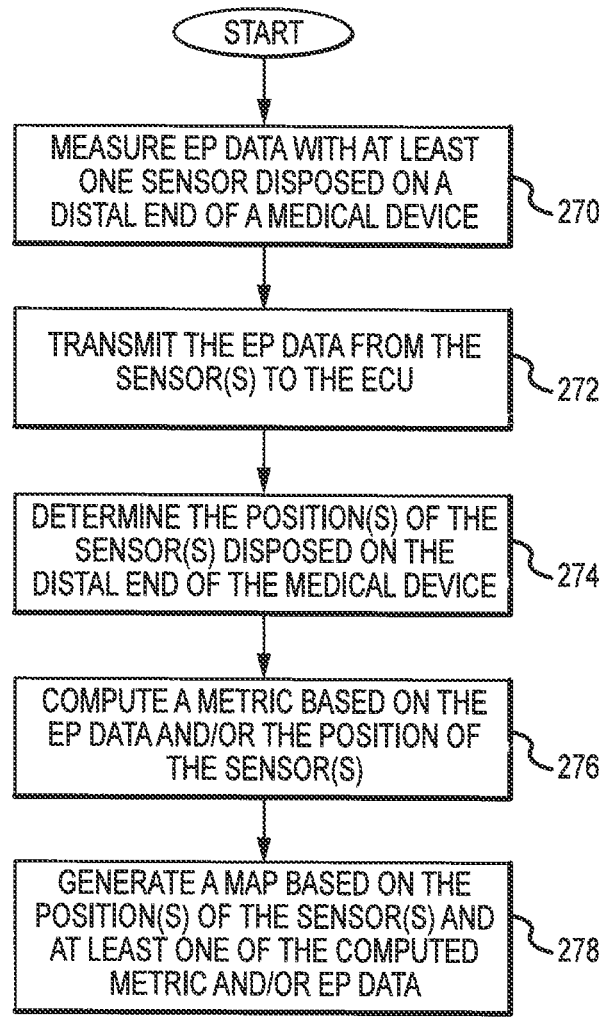
FIG. 17 is a flow diagram showing one embodiment of a method in which a system may measure, analyze, and map spatial electrophysiological patterns.

With reference to FIG. 17, one embodiment of the system 10 may be described generally as follows. At step 270, at least one of a plurality of sensors disposed on a distal end of a medical device may measure EP data. In some embodiments, only one sensor may measure EP data. In other embodiments, though, more than one or even all sensors on the distal end may measure EP data. In still further embodiments, sensors from numerous medical devices may be simultaneously measuring EP data.

At step 272, the ECU may acquire the EP data that is transmitted from at least one of the sensors. To that end, the sensors may be operably and electrically coupled to the ECU. Further, the ECU may in some instances continuously acquire EP data as measured by the sensors.

Once the ECU has acquired the EP data, the system 10 may at step 274 determine positions of one or more of the plurality of sensors disposed on the distal end of the medical device. As described above, the system 10 may use the visualization, navigation, and mapping subsystem to help determine the positions of the sensors. The positions are important for a number of reasons, including that the system 10 may associate EP data values with particular locations from which the EP data is measured.

At step 276, the system 10 may compute one or more metrics based on the EP data and/or based on the position(s) of the sensor(s) that measured EP data. For example, the system computes some metrics based on both the spacing between the sensors and the EP data values at those sensors. Other metrics are based solely on the EP data values acquired from one or more sensors. In any event, the metric(s) may be any one of the exemplary metrics disclosed above or may be a combination or derivation of the metrics described above.

The system 10 at step 278 may be configured to generate a map based on the position of at least one of the sensors that measured EP data and also based on either the EP data measured by the sensor or the metric computed in step 276. In short, the system 10 may display the EP data value(s) or the computed metric value(s) at the location from which the sensor measured the data. Where numerous sensors measure EP data, the system 10 may generate maps that depict the spatial variation in EP data or metric values across or throughout an object from which the EP data was measured.

As briefly mentioned above, it will be appreciated that additional functionality described in greater detail above with respect to the system 10 may also be part of the inventive methodology. Therefore, to the extent such functionality has not been expressly described with respect to the methodology, the description thereof above is incorporated herein by reference.

Further, it should be understood that the system 10, and particularly the ECU 100, as described above may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosed system and methods. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosed system and methods as defined in the appended claims.

What is claimed:

1. A system for determining electrophysiological (EP) data from a tissue of a body, the system comprising:
   a processor; and
   a non-transitory computer readable medium coupled with the processor, the non-transitory computer readable medium storing instructions executable by the processor to:
   receive EP data from a plurality of points located on the tissue of the body from a plurality of sensors;
   compute an absolute activation time for each of the plurality of points based on the EP data: and
   cause the EP data to be displayed to a user on a display device, wherein the EP data is associated with the absolute activation time.

2. The system of claim 1, further comprising instructions executable by the processor to compute a vector that represents a direction and velocity magnitude of a depolarization wavefront traversing the tissue of the body based on the EP data received from the plurality of sensors.

3. The system of claim 2, further comprising instructions executable to generate a map based on the absolute activation time for each of the plurality of points.

4. The system of claim 1, wherein the absolute activation time is indicative of an amount of time that has elapsed since a most recent activation at each point.

5. The system of claim 4, wherein the plurality of sensors include a plurality of electrodes and the absolute activation time is indicative of an amount of time that has elapse since a most recent activation at each of the plurality of electrodes.

6. The system of claim 1, further comprising instructions executable to generate a gradient map of conduction velocity based on the EP data.

7. The system of claim 1, further comprising instructions executable to generate a gradient map of activation amplitude based on the EP data.

8. The system of claim 1, further comprising instructions executable to determine a time at which each of the points is activated based on the EP data.

9. The system of claim 1, further comprising instructions executable to compute a derivative metric based on the EP data.

10. A method, comprising:
   receiving EP data from a plurality of points located on a tissue of a body from a plurality of sensors;
   computing an amount of time that has elapsed since a most recent activation at each of the plurality of points; and
   generate an absolute activation time map based on the amount of time that has elapsed since a most recent activation at each of the plurality of points.

11. The method of claim 10, further comprising computing an amount of time that has elapsed since each of the plurality of sensors was last depolarized.

12. The method of claim 10, further comprising computing an amount of time that the sensor spends depolarizing.

13. The method of claim 10, further comprising determining a vector representative of an activation at each of the plurality of points based on the EP data.

14. The method of claim 13, wherein the vector represents a wavefront associated with the activation for one of the sensors.

15. The method of claim 13, wherein the vector represents a wavefront associated with the activation for a subset of the plurality of sensors.

16. A system for determining electrophysiological (EP) data from a tissue of a body, the system comprising:
   a processor; and
   a non-transitory computer readable medium coupled with the processor, the non-transitory computer readable medium storing instructions executable by the processor to:
   receive EP data from a plurality of points located on the tissue of the body from a plurality of sensors;
   calculate a first plurality of absolute activation times based on the received EP data;
   calculate a second plurality of absolute activation times based on the received EP data;
   determine a first depolarization wavefront based on the first plurality of activation times;
   determine a second depolarization wavefront based on the second plurality of activation times: and
   cause a wavefront pattern to be displayed, on a display device, based on at least one of the first depolarization wavefront and the second depolarization wavefront.

17. The system of claim 16, wherein the absolute activation time is defined as an amount of time that has elapsed since a most recent activation at each of the plurality of points.

18. The system of claim 17, further comprising determining a depolarization amplitude voltage, the depolarization amplitude voltage being defined as an amount of change between a highest peak voltage and a lowest trough voltage experienced by a specific point on the tissue during the depolarization wavefront.

19. The system of claim 16, further comprising instructions executable to define a time interval during which the EP data is collected from the plurality of points located on the tissue of the body.

* * * * *